United States Patent
Zhou et al.

(10) Patent No.: US 11,951,173 B2
(45) Date of Patent: Apr. 9, 2024

(54) TETRAVALENT ANTIBODY-DRUG CONJUGATES AND USE THEREOF

(71) Applicant: Bliss Biopharmaceutical (Hangzhou) Co., Ltd., Hangzhou (CN)

(72) Inventors: Yuhong Zhou, Phoenixville, PA (US); Ziping Wei, North Potomac, MD (US)

(73) Assignee: Bliss Biopharmaceutical (Hangzhou) Co., Ltd., Hangzhou (CN)

( * ) Notice: Subject to any disclaimer, the term of this patent is extended or adjusted under 35 U.S.C. 154(b) by 547 days.

(21) Appl. No.: 17/227,536

(22) Filed: Apr. 12, 2021

(65) Prior Publication Data

US 2021/0346510 A1    Nov. 11, 2021

Related U.S. Application Data

(63) Continuation of application No. 16/862,042, filed on Apr. 29, 2020, now Pat. No. 10,994,021.

(60) Provisional application No. 63/008,726, filed on Apr. 11, 2020.

(51) Int. Cl.
*A61K 47/68* (2017.01)
*A61K 47/60* (2017.01)
*C07K 16/28* (2006.01)
*C07K 16/32* (2006.01)
*C07K 16/46* (2006.01)

(52) U.S. Cl.
CPC .......... *A61K 47/6803* (2017.08); *A61K 47/60* (2017.08); *A61K 47/6849* (2017.08); *C07K 16/2863* (2013.01); *C07K 16/32* (2013.01); *C07K 16/468* (2013.01); *C07K 2317/35* (2013.01)

(58) Field of Classification Search
None
See application file for complete search history.

(56) References Cited

FOREIGN PATENT DOCUMENTS

WO    WO-2018191188 A1 * 10/2018 ............. A61P 35/00

* cited by examiner

*Primary Examiner* — Brad Duffy
(74) *Attorney, Agent, or Firm* — Yong Chen; Lin Sun-Hoffman; Liu Chen & Hoffman LLP

(57) ABSTRACT

An antibody-drug conjugate (ADC) or a pharmaceutically acceptable salt thereof, is provided. The ADC includes a tetravalent monoclonal antibody conjugated to a cytotoxic drug by a chemical linker. The monoclonal antibody includes two long chains and four short chains. Each of the long chains includes a first segment and a second segment, the first segment located proximal to the N-terminus of the long chain, and the second segment located proximal to the C-terminus of the long chain. Each of the first segment and second segment pairs with one of the short chains to form an antigen-binding fragment domain, therefore forming four antigen-binding fragment domains having specificity toward the same antigen. Pharmaceutical composition including the ADC and methods of treating diseases using the compositions are also provided.

13 Claims, 7 Drawing Sheets

Specification includes a Sequence Listing.

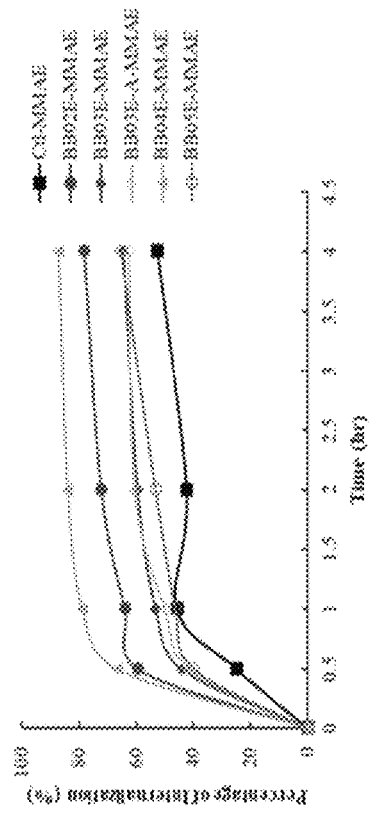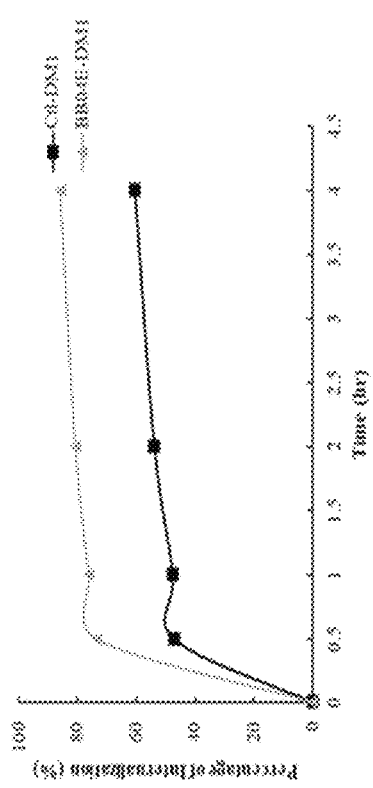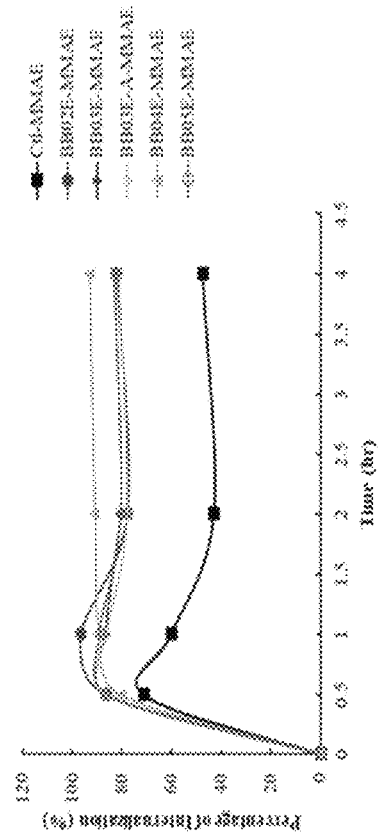
FIG. 6A
FIG. 6B
FIG. 6C

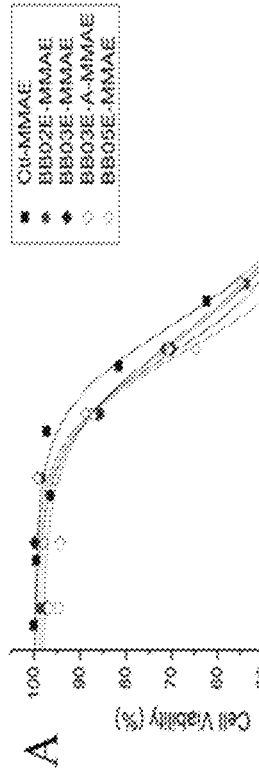
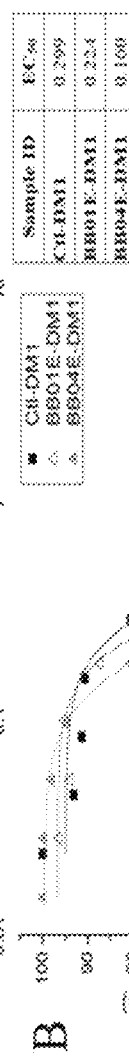
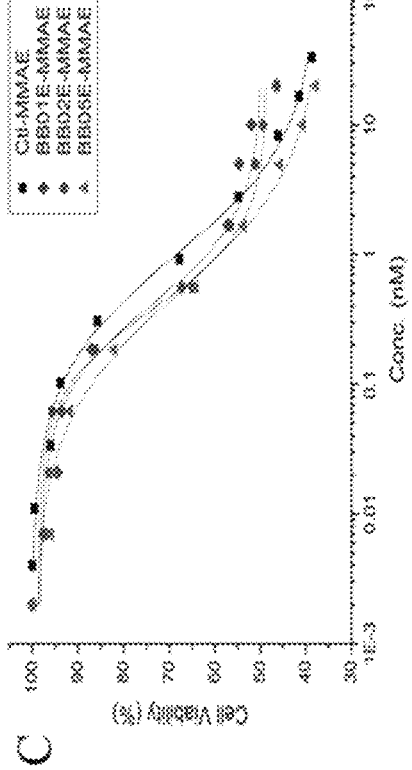
FIG. 7A
FIG. 7B
FIG. 7C

SEQUENCE LISTING

<160> NUMBER OF SEQ ID NOS: 64

<210> SEQ ID NO 1
<211> LENGTH: 689
<212> TYPE: PRT

<213> ORGANISM: Artificial Sequence
<220> FEATURE:
<223> OTHER INFORMATION: Synthetic

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

```
                385                 390                 395                 400
Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys Gly Gly Gly Ser Gly Gly Gly Ser Gly Gly Gly Ser Gly Gly
        450                 455                 460

Gly Ser Glu Val Gln Leu Val Glu Ser Gly Gly Leu Val Gln Pro
465                 470                 475                 480

Gly Gly Ser Leu Arg Leu Ser Cys Ala Ala Ser Gly Phe Asn Ile Lys
                485                 490                 495

Asp Thr Tyr Ile His Trp Val Arg Gln Ala Pro Gly Lys Gly Leu Glu
                500                 505                 510

Trp Val Ala Arg Ile Tyr Pro Thr Asn Gly Tyr Thr Arg Tyr Ala Asp
            515                 520                 525

Ser Val Lys Gly Arg Phe Thr Ile Ser Ala Asp Thr Ser Lys Asn Thr
        530                 535                 540

Ala Tyr Leu Gln Met Asn Ser Leu Arg Ala Glu Asp Thr Ala Val Tyr
545                 550                 555                 560

Tyr Cys Ser Arg Trp Gly Gly Asp Gly Phe Tyr Ala Met Asp Tyr Trp
                565                 570                 575

Gly Gln Gly Thr Leu Val Thr Val Ser Ser Ala Ser Thr Lys Gly Pro
                580                 585                 590

Ser Val Phe Pro Leu Ala Pro Ser Ser Lys Ser Thr Ser Gly Gly Thr
            595                 600                 605

Ala Ala Leu Gly Cys Leu Val Lys Asp Tyr Phe Pro Glu Pro Val Thr
        610                 615                 620

Val Ser Trp Asn Ser Gly Ala Leu Thr Ser Gly Val His Thr Phe Pro
625                 630                 635                 640

Ala Val Leu Gln Ser Ser Gly Leu Tyr Ser Leu Ser Ser Val Val Thr
                645                 650                 655

Val Pro Ser Ser Ser Leu Gly Thr Gln Thr Tyr Ile Cys Asn Val Asn
                660                 665                 670

His Lys Pro Ser Asn Thr Lys Val Asp Lys Arg Val Glu Pro Lys Ser
            675                 680                 685

Cys

<210> SEQ ID NO 2
<211> LENGTH: 214
<212> TYPE: PRT
<213> ORGANISM: Artificial Sequence
<220> FEATURE:
<223> OTHER INFORMATION: Synthetic

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 678
<212> TYPE: PRT
<213> ORGANISM: Artificial Sequence
<220> FEATURE:
<223> OTHER INFORMATION: Synthetic

<400> SEQUENCE: 3

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205
```

-continued

Ser Asn Thr Lys Val Asp Lys Thr Val Glu Arg Lys Cys Cys Val Glu
    210             215                 220

Cys Pro Pro Cys Pro Ala Pro Pro Val Ala Gly Pro Ser Val Phe Leu
225             230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305             310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
            355                 360                 365

Gly Phe Tyr Pro Ser Asp Ile Ser Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
            435                 440                 445

Ser Gly Gly Gly Ser Gly Gly Gly Ser Gly Gly Ser Gln Val Gln
450                 455                 460

Leu Lys Gln Ser Gly Pro Gly Leu Val Gln Pro Ser Gln Ser Leu Ser
465                 470                 475                 480

Ile Thr Cys Thr Val Ser Gly Phe Ser Leu Thr Asn Tyr Gly Val His
                485                 490                 495

Trp Val Arg Gln Ser Pro Gly Lys Gly Leu Glu Trp Leu Gly Val Ile
            500                 505                 510

Trp Ser Gly Gly Asn Thr Asp Tyr Asn Thr Pro Phe Thr Ser Arg Leu
            515                 520                 525

Ser Ile Asn Lys Asp Asn Ser Lys Ser Gln Val Phe Phe Lys Met Asn
530                 535                 540

Ser Leu Gln Ser Asn Asp Thr Ala Ile Tyr Tyr Cys Ala Arg Ala Leu
545                 550                 555                 560

Thr Tyr Tyr Asp Tyr Glu Phe Ala Tyr Trp Gly Gln Gly Thr Leu Val
                565                 570                 575

Thr Val Ser Ala Ala Ser Thr Lys Gly Pro Ser Val Phe Pro Leu Ala
            580                 585                 590

Pro Cys Ser Arg Ser Thr Ser Glu Ser Thr Ala Ala Leu Gly Cys Leu
            595                 600                 605

Val Lys Asp Tyr Phe Pro Glu Pro Val Thr Val Ser Trp Asn Ser Gly
610                 615                 620

```
Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Asn Phe
            645                 650                 655

Gly Thr Gln Thr Tyr Thr Cys Asn Val Asp His Lys Pro Ser Asn Thr
        660                 665                 670

Lys Val Asp Lys Thr Val
        675

<210> SEQ ID NO 4
<211> LENGTH: 213
<212> TYPE: PRT
<213> ORGANISM: Artificial Sequence
<220> FEATURE:
<223> OTHER INFORMATION: Synthetic

<400> SEQUENCE: 4

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Gly Gln Pro Lys Ala
            100                 105                 110

Asn Pro Thr Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Gly Ser Pro Val Lys Ala Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 5
<211> LENGTH: 687
<212> TYPE: PRT
<213> ORGANISM: Artificial Sequence
<220> FEATURE:
<223> OTHER INFORMATION: Synthetic

<400> SEQUENCE: 5

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30
```

-continued

Gly Val His Trp Val Arg Gln Ser Pro Gly Lys Gly Leu Glu Trp Leu
          35                  40                  45
Gly Val Ile Trp Ser Gly Gly Asn Thr Asp Tyr Asn Thr Pro Phe Thr
 50                  55                  60
Ser Arg Leu Ser Ile Asn Lys Asp Asn Ser Lys Ser Gln Val Phe Phe
 65                  70                  75                  80
Lys Met Asn Ser Leu Gln Ser Asp Asp Thr Ala Ile Tyr Tyr Cys Ala
                 85                  90                  95
Arg Ala Leu Thr Tyr Tyr Asp Tyr Glu Phe Ala Tyr Trp Gly Gln Gly
                100                 105                 110
Thr Leu Val Thr Val Ser Ala Ala Ser Thr Lys Gly Pro Ser Val Phe
                115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
        435                 440                 445

Lys Gly Gly Ser Gly Gly Gly Ser Gly Gly Gly Gly
    450             455             460

Ser Gln Val Gln Leu Lys Gln Ser Gly Pro Gly Leu Val Gln Pro Ser
465                 470                 475                 480

Gln Ser Leu Ser Ile Thr Cys Thr Val Ser Gly Phe Ser Leu Thr Asn
            485                 490                 495

Tyr Gly Val His Trp Val Arg Gln Ser Pro Gly Lys Gly Leu Glu Trp
            500                 505                 510

Leu Gly Val Ile Trp Ser Gly Gly Asn Thr Asp Tyr Asn Thr Pro Phe
            515                 520                 525

Thr Ser Arg Leu Ser Ile Asn Lys Asp Asn Ser Lys Ser Gln Val Phe
530                 535                 540

Phe Lys Met Asn Ser Leu Gln Ser Asp Asp Thr Ala Ile Tyr Tyr Cys
545                 550                 555                 560

Ala Arg Ala Leu Thr Tyr Tyr Asp Tyr Glu Phe Ala Tyr Trp Gly Gln
                565                 570                 575

Gly Thr Leu Val Thr Val Ser Ala Ala Ser Thr Lys Gly Pro Ser Val
            580                 585                 590

Phe Pro Leu Ala Pro Ser Ser Lys Ser Thr Ser Gly Gly Thr Ala Ala
            595                 600                 605

Leu Gly Cys Leu Val Lys Asp Tyr Phe Pro Glu Pro Val Thr Val Ser
610                 615                 620

Trp Asn Ser Gly Ala Leu Thr Ser Gly Val His Thr Phe Pro Ala Val
625                 630                 635                 640

Leu Gln Ser Ser Gly Leu Tyr Ser Leu Ser Ser Val Val Thr Val Pro
                645                 650                 655

Ser Ser Ser Leu Gly Thr Gln Thr Tyr Ile Cys Asn Val Asn His Lys
            660                 665                 670

Pro Ser Asn Thr Lys Val Asp Lys Arg Val Glu Pro Lys Ser Cys
            675                 680                 685

<210> SEQ ID NO 6
<211> LENGTH: 214
<212> TYPE: PRT
<213> ORGANISM: Artificial Sequence
<220> FEATURE:
<223> OTHER INFORMATION: Synthetic

<400> SEQUENCE: 6

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 7
<211> LENGTH: 687
<212> TYPE: PRT
<213> ORGANISM: Artificial Sequence
<220> FEATURE:
<223> OTHER INFORMATION: Synthetic

<400> SEQUENCE: 7

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Val Ser Ser Gly
            20                  25                  30
Asp Tyr Tyr Trp Thr Trp Ile Arg Gln Ser Pro Gly Lys Gly Leu Glu
        35                  40                  45
Trp Ile Gly His Ile Tyr Tyr Ser Gly Asn Thr Asn Tyr Asn Pro Ser
    50                  55                  60
Leu Lys Ser Arg Leu Thr Ile Ser Ile Asp Thr Ser Lys Thr Gln Phe
65                  70                  75                  80
Ser Leu Lys Leu Ser Ser Val Thr Ala Ala Asp Thr Ala Ile Tyr Tyr
                85                  90                  95
Cys Val Arg Asp Arg Val Thr Gly Ala Phe Asp Ile Trp Gly Gln Gly
            100                 105                 110
Thr Met Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Ser Gly Gly Gly Ser Gly Gly Gly Ser Gly Gly Gly
            450                 455                 460

Ser Gln Val Gln Leu Gln Glu Ser Gly Pro Gly Leu Val Lys Pro Ser
465                 470                 475                 480

Glu Thr Leu Ser Leu Thr Cys Thr Val Ser Gly Gly Ser Val Ser Ser
                485                 490                 495

Gly Asp Tyr Tyr Trp Thr Trp Ile Arg Gln Ser Pro Gly Lys Gly Leu
                500                 505                 510

Glu Trp Ile Gly His Ile Tyr Tyr Ser Gly Asn Thr Asn Tyr Asn Pro
            515                 520                 525

Ser Leu Lys Ser Arg Leu Thr Ile Ser Ile Asp Thr Ser Lys Thr Gln
            530                 535                 540

Phe Ser Leu Lys Leu Ser Ser Val Thr Ala Ala Asp Thr Ala Ile Tyr
545                 550                 555                 560

Tyr Cys Val Arg Asp Arg Val Thr Gly Ala Phe Asp Ile Trp Gly Gln
                565                 570                 575

Gly Thr Met Val Thr Val Ser Ser Ala Ser Thr Lys Gly Pro Ser Val
            580                 585                 590

Phe Pro Leu Ala Pro Ser Ser Lys Ser Thr Ser Gly Gly Thr Ala Ala
            595                 600                 605

Leu Gly Cys Leu Val Lys Asp Tyr Phe Pro Glu Pro Val Thr Val Ser
    610                 615                 620

Trp Asn Ser Gly Ala Leu Thr Ser Gly Val His Thr Phe Pro Ala Val
625                 630                 635                 640

Leu Gln Ser Ser Gly Leu Tyr Ser Leu Ser Ser Val Val Thr Val Pro
                645                 650                 655

Ser Ser Ser Leu Gly Thr Gln Thr Tyr Ile Cys Asn Val Asn His Lys
            660                 665                 670

Pro Ser Asn Thr Lys Val Asp Lys Arg Val Glu Pro Lys Ser Cys
            675                 680                 685
```

```
<210> SEQ ID NO 8
<211> LENGTH: 214
<212> TYPE: PRT
<213> ORGANISM: Artificial Sequence
<220> FEATURE:
<223> OTHER INFORMATION: Synthetic

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 666
<212> TYPE: PRT
<213> ORGANISM: Artificial Sequence
<220> FEATURE:
<223> OTHER INFORMATION: Synthetic

<400> SEQUENCE: 9

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
50                  55                  60

Ser Arg Leu Ser Ile Asn Lys Asp Asn Ser Lys Ser Gln Val Phe Phe
65                  70                  75                  80

Lys Met Asn Ser Leu Gln Ser Asp Asp Thr Ala Ile Tyr Tyr Cys Ala
                85                  90                  95
```

-continued

```
Arg Ala Leu Thr Tyr Tyr Asp Tyr Glu Phe Ala Tyr Trp Gly Gln Gly
                100             105             110

Thr Leu Val Thr Val Ser Ala Ala Ser Thr Lys Gly Pro Ser Val Phe
        115                 120             125

Pro Leu Ala Pro Cys Ser Arg Ser Thr Ser Glu Ser Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
        180             185             190

Ser Asn Phe Gly Thr Gln Thr Tyr Thr Cys Asn Val Asp His Lys Pro
    195             200             205

Ser Asn Thr Lys Val Asp Lys Thr Val Glu Arg Lys Cys Cys Val Glu
    210             215             220

Cys Pro Pro Cys Pro Ala Pro Pro Val Ala Gly Pro Ser Val Phe Leu
225             230             235             240

Phe Pro Pro Lys Pro Lys Asp Thr Leu Met Ile Ser Arg Thr Pro Glu
            245             250             255

Val Thr Cys Val Val Val Asp Val Ser His Glu Asp Pro Glu Val Gln
        260             265             270

Phe Asn Trp Tyr Val Asp Gly Val Glu Val His Asn Ala Lys Thr Lys
    275             280             285

Pro Arg Glu Glu Gln Phe Asn Ser Thr Phe Arg Val Val Ser Val Leu
    290             295             300

Thr Val Val His Gln Asp Trp Leu Asn Gly Lys Glu Tyr Lys Cys Lys
305             310             315             320

Val Ser Asn Lys Gly Leu Pro Ala Pro Ile Glu Lys Thr Ile Ser Lys
            325             330             335

Thr Lys Gly Gln Pro Arg Glu Pro Gln Val Tyr Thr Leu Pro Pro Ser
        340             345             350

Arg Glu Glu Met Thr Lys Asn Gln Val Ser Leu Thr Cys Leu Val Lys
    355             360             365

Gly Phe Tyr Pro Ser Asp Ile Ser Val Glu Trp Glu Ser Asn Gly Gln
    370             375             380

Pro Glu Asn Asn Tyr Lys Thr Thr Pro Pro Met Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
        420             425             430

His Tyr Thr Gln Lys Ser Leu Ser Leu Ser Pro Gly Lys Gly Gly Gly
    435             440             445

Ser Gln Val Gln Leu Lys Gln Ser Gly Pro Gly Leu Val Gln Pro Ser
    450             455             460

Gln Ser Leu Ser Ile Thr Cys Thr Val Ser Gly Phe Ser Leu Thr Asn
465             470             475             480

Tyr Gly Val His Trp Val Arg Gln Ser Pro Gly Lys Gly Leu Glu Trp
            485             490             495

Leu Gly Val Ile Trp Ser Gly Gly Asn Thr Asp Tyr Asn Thr Pro Phe
        500             505             510

Thr Ser Arg Leu Ser Ile Asn Lys Asp Asn Ser Lys Ser Gln Val Phe
```

```
                515                 520                 525
    Phe Lys Met Asn Ser Leu Gln Ser Asp Asp Thr Ala Ile Tyr Tyr Cys
        530                 535                 540

Ala Arg Ala Leu Thr Tyr Tyr Asp Tyr Glu Phe Ala Tyr Trp Gly Gln
    545                 550                 555                 560

Gly Thr Leu Val Thr Val Ser Ala Ala Ser Thr Lys Gly Pro Ser Val
                        565                 570                 575

Phe Pro Leu Ala Pro Cys Ser Arg Ser Thr Ser Glu Ser Thr Ala Ala
                    580                 585                 590

Leu Gly Cys Leu Val Lys Asp Tyr Phe Pro Glu Pro Val Thr Val Ser
                595                 600                 605

Trp Asn Ser Gly Ala Leu Thr Ser Gly Val His Thr Phe Pro Ala Val
            610                 615                 620

Leu Gln Ser Ser Gly Leu Tyr Ser Leu Ser Ser Val Val Thr Val Pro
    625                 630                 635                 640

Ser Ser Asn Phe Gly Thr Gln Thr Tyr Thr Cys Asn Val Asp His Lys
                        645                 650                 655

Pro Ser Asn Thr Lys Val Asp Lys Thr Val
                    660                 665

<210> SEQ ID NO 10
<211> LENGTH: 214
<212> TYPE: PRT
<213> ORGANISM: Artificial Sequence
<220> FEATURE:
<223> OTHER INFORMATION: Synthetic

<400> SEQUENCE: 10

Asp Ile Leu Leu Thr Gln Ser Pro Val Ile Leu Ser Val Ser Pro Gly
    1               5                   10                  15

Glu Arg Val Ser Phe Ser Cys Arg Ala Ser Gln Ser Ile Gly Thr Asn
                    20                  25                  30

Ile His Trp Tyr Gln Gln Arg Thr Asn Gly Ser Pro Arg Leu Leu Ile
                35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
    65                  70                  75                  80

Glu Asp Ile Ala Asp Tyr Tyr Cys Gln Gln Asn Asn Asn Trp Pro Thr
                    85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
    145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
```

-continued

210

<210> SEQ ID NO 11
<211> LENGTH: 671
<212> TYPE: PRT
<213> ORGANISM: Artificial Sequence
<220> FEATURE:
<223> OTHER INFORMATION: Synthetic

<400> SEQUENCE: 11

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Trp Pro Thr
                85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro

```
                355                 360                 365
Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Gly Gly Ser Gly Gly Gly
        435                 440                 445

Ser Gly Gly Gly Ser Gly Gly Gly Ser Asp Ile Leu Leu Thr Gln Ser
    450                 455                 460

Pro Val Ile Leu Ser Val Ser Pro Gly Glu Arg Val Ser Phe Ser Cys
465                 470                 475                 480

Arg Ala Ser Gln Ser Ile Gly Thr Asn Ile His Trp Tyr Gln Gln Arg
                485                 490                 495

Thr Asn Gly Ser Pro Arg Leu Leu Ile Lys Tyr Ala Ser Glu Ser Ile
            500                 505                 510

Ser Gly Ile Pro Ser Arg Phe Ser Gly Ser Gly Ser Gly Thr Asp Phe
        515                 520                 525

Thr Leu Ser Ile Asn Ser Val Glu Ser Glu Asp Ile Ala Asp Tyr Tyr
    530                 535                 540

Cys Gln Gln Asn Asn Asn Trp Pro Thr Thr Phe Gly Ala Gly Thr Lys
545                 550                 555                 560

Leu Glu Leu Lys Arg Thr Val Ala Ala Pro Ser Val Phe Ile Phe Pro
                565                 570                 575

Pro Ser Asp Glu Gln Leu Lys Ser Gly Thr Ala Ser Val Val Cys Leu
            580                 585                 590

Leu Asn Asn Phe Tyr Pro Arg Glu Ala Lys Val Gln Trp Lys Val Asp
        595                 600                 605

Asn Ala Leu Gln Ser Gly Asn Ser Gln Glu Ser Val Thr Glu Gln Asp
    610                 615                 620

Ser Lys Asp Ser Thr Tyr Ser Leu Ser Ser Thr Leu Thr Leu Ser Lys
625                 630                 635                 640

Ala Asp Tyr Glu Lys His Lys Val Tyr Ala Cys Glu Val Thr His Gln
                645                 650                 655

Gly Leu Ser Ser Pro Val Thr Lys Ser Phe Asn Arg Gly Glu Cys
            660                 665                 670

<210> SEQ ID NO 12
<211> LENGTH: 222
<212> TYPE: PRT
<213> ORGANISM: Artificial Sequence
<220> FEATURE:
<223> OTHER INFORMATION: Synthetic

<400> SEQUENCE: 12

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
```

```
                    50                  55                  60
Ser Arg Leu Ser Ile Asn Lys Asp Asn Ser Lys Ser Gln Val Phe Phe
 65                  70                  75                  80

Lys Met Asn Ser Leu Gln Ser Asp Asp Thr Ala Ile Tyr Tyr Cys Ala
                    85                  90                  95

Arg Ala Leu Thr Tyr Tyr Asp Tyr Glu Phe Ala Tyr Trp Gly Gln Gly
                   100                 105                 110

Thr Leu Val Thr Val Ser Ala Ala Ser Thr Lys Gly Pro Ser Val Phe
                   115                 120                 125

Pro Leu Ala Pro Ser Ser Lys Ser Thr Ser Gly Gly Thr Ala Ala Leu
                   130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                   165                 170                 175

Gln Ser Ser Gly Leu Tyr Ser Leu Ser Ser Val Val Thr Val Pro Ser
                   180                 185                 190

Ser Ser Leu Gly Thr Gln Thr Tyr Ile Cys Asn Val Asn His Lys Pro
                   195                 200                 205

Ser Asn Thr Lys Val Asp Lys Arg Val Glu Pro Lys Ser Cys
                   210                 215                 220
```

<210> SEQ ID NO 13
<211> LENGTH: 688
<212> TYPE: PRT
<213> ORGANISM: Artificial Sequence
<220> FEATURE:
<223> OTHER INFORMATION: Synthetic

<400> SEQUENCE: 13

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
                    20                  25                  30

Thr Met Asp Trp Val Arg Gln Ala Pro Gly Lys Gly Leu Glu Trp Val
                    35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Asn Leu Gly Pro Ser Phe Tyr Phe Asp Tyr Trp Gly Gln Gly
                   100                 105                 110

Thr Leu Val Thr Val Ser Ser Ala Ser Thr Lys Gly Pro Ser Val Phe
                   115                 120                 125

Pro Leu Ala Pro Ser Ser Lys Ser Thr Ser Gly Gly Thr Ala Ala Leu
                   130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                   165                 170                 175

Gln Ser Ser Gly Leu Tyr Ser Leu Ser Ser Val Val Thr Val Pro Ser
                   180                 185                 190

Ser Ser Leu Gly Thr Gln Thr Tyr Ile Cys Asn Val Asn His Lys Pro
```

```
            195                 200                 205
Ser Asn Thr Lys Val Asp Lys Arg Val Glu Pro Lys Ser Cys Asp Lys
            210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Ser Gly Gly Gly Ser Gly Gly Gly Ser Gly Gly Gly
            450                 455                 460

Ser Glu Val Gln Leu Val Glu Ser Gly Gly Gly Leu Val Gln Pro Gly
465                 470                 475                 480

Gly Ser Leu Arg Leu Ser Cys Ala Ala Ser Gly Phe Asn Ile Lys Asp
                485                 490                 495

Thr Tyr Ile His Trp Val Arg Gln Ala Pro Gly Lys Gly Leu Glu Trp
                500                 505                 510

Val Ala Arg Ile Tyr Pro Thr Asn Gly Tyr Thr Arg Tyr Ala Asp Ser
            515                 520                 525

Val Lys Gly Arg Phe Thr Ile Ser Ala Asp Thr Ser Lys Asn Thr Ala
            530                 535                 540

Tyr Leu Gln Met Asn Ser Leu Arg Ala Glu Asp Thr Ala Val Tyr Tyr
545                 550                 555                 560

Cys Ser Arg Trp Gly Gly Asp Gly Phe Tyr Ala Met Asp Tyr Trp Gly
                565                 570                 575

Gln Gly Thr Leu Val Thr Val Ser Ser Ala Ser Thr Lys Gly Pro Ser
                580                 585                 590

Val Phe Pro Leu Ala Pro Ser Ser Lys Ser Thr Ser Gly Gly Thr Ala
            595                 600                 605

Ala Leu Gly Cys Leu Val Lys Asp Tyr Phe Pro Glu Pro Val Thr Val
            610                 615                 620
```

Ser Trp Asn Ser Gly Ala Leu Thr Ser Gly Val His Thr Phe Pro Ala
625                 630                 635                 640

Val Leu Gln Ser Ser Gly Leu Tyr Ser Leu Ser Ser Val Val Thr Val
            645                 650                 655

Pro Ser Ser Leu Gly Thr Gln Thr Tyr Ile Cys Asn Val Asn His
            660                 665                 670

Lys Pro Ser Asn Thr Lys Val Asp Lys Arg Val Glu Pro Lys Ser Cys
        675                 680                 685

<210> SEQ ID NO 14
<211> LENGTH: 214
<212> TYPE: PRT
<213> ORGANISM: Artificial Sequence
<220> FEATURE:
<223> OTHER INFORMATION: Synthetic

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 671
<212> TYPE: PRT
<213> ORGANISM: Artificial Sequence
<220> FEATURE:
<223> OTHER INFORMATION: Synthetic

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly

-continued

```
                20                  25                  30
Val Ala Trp Tyr Gln Gln Lys Pro Gly Lys Ala Pro Lys Leu Leu Ile
            35                  40                  45
Tyr Ser Ala Ser Tyr Arg Tyr Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Ile Tyr Pro Tyr
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
    115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
    195                 200                 205
Phe Asn Arg Gly Glu Cys Asp Lys Thr His Thr Cys Pro Pro Cys Pro
    210                 215                 220
Ala Pro Glu Ala Ala Gly Gly Pro Ser Val Phe Leu Phe Pro Pro Lys
225                 230                 235                 240
Pro Lys Asp Thr Leu Met Ile Ser Arg Thr Pro Glu Val Thr Cys Val
                245                 250                 255
Val Val Asp Val Ser His Glu Asp Pro Glu Val Lys Phe Asn Trp Tyr
            260                 265                 270
Val Asp Gly Val Glu Val His Asn Ala Lys Thr Lys Pro Arg Glu Glu
    275                 280                 285
Gln Tyr Asn Ser Thr Tyr Arg Val Val Ser Val Leu Thr Val Leu His
    290                 295                 300
Gln Asp Trp Leu Asn Gly Lys Glu Tyr Lys Cys Lys Val Ser Asn Lys
305                 310                 315                 320
Ala Leu Pro Ala Pro Ile Glu Lys Thr Ile Ser Lys Ala Lys Gly Gln
                325                 330                 335
Pro Arg Glu Pro Gln Val Tyr Thr Leu Pro Pro Ser Arg Glu Glu Met
            340                 345                 350
Thr Lys Asn Gln Val Ser Leu Thr Cys Leu Val Lys Gly Phe Tyr Pro
    355                 360                 365
Ser Asp Ile Ala Val Glu Trp Glu Ser Asn Gly Gln Pro Glu Asn Asn
    370                 375                 380
Tyr Lys Thr Thr Pro Pro Val Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
Phe Ser Cys Ser Val Met His Glu Ala Leu His Asn His Tyr Thr Gln
            420                 425                 430
Lys Ser Leu Ser Leu Ser Pro Gly Lys Gly Gly Gly Ser Gly Gly Gly
    435                 440                 445
```

Ser Gly Gly Gly Ser Gly Gly Gly Ser Asp Ile Gln Met Thr Gln Ser
            450                 455                 460

Pro Ser Ser Leu Ser Ala Ser Val Gly Asp Arg Val Thr Ile Thr Cys
465                 470                 475                 480

Lys Ala Ser Gln Asp Val Ser Ile Gly Val Ala Trp Tyr Gln Gln Lys
                485                 490                 495

Pro Gly Lys Ala Pro Lys Leu Leu Ile Tyr Ser Ala Ser Tyr Arg Tyr
            500                 505                 510

Thr Gly Val Pro Ser Arg Phe Ser Gly Ser Gly Ser Gly Thr Asp Phe
            515                 520                 525

Thr Leu Thr Ile Ser Ser Leu Gln Pro Glu Asp Phe Ala Thr Tyr Tyr
            530                 535                 540

Cys Gln Gln Tyr Tyr Ile Tyr Pro Tyr Thr Phe Gly Gln Gly Thr Lys
545                 550                 555                 560

Val Glu Ile Lys Arg Thr Val Ala Ala Pro Ser Val Phe Ile Phe Pro
                565                 570                 575

Pro Ser Asp Glu Gln Leu Lys Ser Gly Thr Ala Ser Val Val Cys Leu
            580                 585                 590

Leu Asn Asn Phe Tyr Pro Arg Glu Ala Lys Val Gln Trp Lys Val Asp
            595                 600                 605

Asn Ala Leu Gln Ser Gly Asn Ser Gln Glu Ser Val Thr Glu Gln Asp
            610                 615                 620

Ser Lys Asp Ser Thr Tyr Ser Leu Ser Ser Thr Leu Thr Leu Ser Lys
625                 630                 635                 640

Ala Asp Tyr Glu Lys His Lys Val Tyr Ala Cys Glu Val Thr His Gln
                645                 650                 655

Gly Leu Ser Ser Pro Val Thr Lys Ser Phe Asn Arg Gly Glu Cys
            660                 665                 670

<210> SEQ ID NO 16
<211> LENGTH: 222
<212> TYPE: PRT
<213> ORGANISM: Artificial Sequence
<220> FEATURE:
<223> OTHER INFORMATION: Synthetic

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Cys
210                 215                 220
```

<210> SEQ ID NO 17
<211> LENGTH: 671
<212> TYPE: PRT
<213> ORGANISM: Artificial Sequence
<220> FEATURE:
<223> OTHER INFORMATION: Synthetic

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285
```

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Gly Gly Ser Gly Gly Gly
        435                 440                 445

Ser Gly Gly Gly Ser Gly Gly Gly Ser Asp Ile Gln Met Thr Gln Ser
    450                 455                 460

Pro Ser Ser Leu Ser Ala Ser Val Gly Asp Arg Val Thr Ile Thr Cys
465                 470                 475                 480

Arg Ala Ser Gln Asp Val Asn Thr Ala Val Ala Trp Tyr Gln Gln Lys
                485                 490                 495

Pro Gly Lys Ala Pro Lys Leu Leu Ile Tyr Ser Ala Ser Phe Leu Tyr
            500                 505                 510

Ser Gly Val Pro Ser Arg Phe Ser Gly Ser Arg Ser Gly Thr Asp Phe
        515                 520                 525

Thr Leu Thr Ile Ser Ser Leu Gln Pro Glu Asp Phe Ala Thr Tyr Tyr
    530                 535                 540

Cys Gln Gln His Tyr Thr Thr Pro Pro Thr Phe Gly Gln Gly Thr Lys
545                 550                 555                 560

Val Glu Ile Lys Arg Thr Val Ala Ala Pro Ser Val Phe Ile Phe Pro
                565                 570                 575

Pro Ser Asp Glu Gln Leu Lys Ser Gly Thr Ala Ser Val Val Cys Leu
            580                 585                 590

Leu Asn Asn Phe Tyr Pro Arg Glu Ala Lys Val Gln Trp Lys Val Asp
        595                 600                 605

Asn Ala Leu Gln Ser Gly Asn Ser Gln Glu Ser Val Thr Glu Gln Asp
    610                 615                 620

Ser Lys Asp Ser Thr Tyr Ser Leu Ser Ser Thr Leu Thr Leu Ser Lys
625                 630                 635                 640

Ala Asp Tyr Glu Lys His Lys Val Tyr Ala Cys Glu Val Thr His Gln
                645                 650                 655

Gly Leu Ser Ser Pro Val Thr Lys Ser Phe Asn Arg Gly Glu Cys
            660                 665                 670

<210> SEQ ID NO 18
<211> LENGTH: 223
<212> TYPE: PRT
<213> ORGANISM: Artificial Sequence
<220> FEATURE:

<223> OTHER INFORMATION: Synthetic

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys
    210                 215                 220
```

<210> SEQ ID NO 19
<211> LENGTH: 671
<212> TYPE: PRT
<213> ORGANISM: Artificial Sequence
<220> FEATURE:
<223> OTHER INFORMATION: Synthetic

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys Gly Gly Gly Ser Gly Gly Gly
        435                 440                 445

Ser Gly Gly Gly Ser Gly Gly Gly Ser Asp Ile Gln Met Thr Gln Ser
    450                 455                 460

Pro Ser Ser Leu Ser Ala Ser Val Gly Asp Arg Val Thr Ile Thr Cys
465                 470                 475                 480

Gln Ala Ser Gln Asp Ile Ser Asn Tyr Leu Asn Trp Tyr Gln Gln Lys
                485                 490                 495

Pro Gly Lys Ala Pro Lys Leu Leu Ile Tyr Asp Ala Ser Asn Leu Glu
            500                 505                 510

Thr Gly Val Pro Ser Arg Phe Ser Gly Ser Gly Ser Gly Thr Asp Phe
        515                 520                 525

Thr Phe Thr Ile Ser Ser Leu Gln Pro Glu Asp Ile Ala Thr Tyr Phe
    530                 535                 540
```

```
Cys Gln His Phe Asp His Leu Pro Leu Ala Phe Gly Gly Gly Thr Lys
545                 550                 555                 560

Val Glu Ile Lys Arg Thr Val Ala Ala Pro Ser Val Phe Ile Phe Pro
            565                 570                 575

Pro Ser Asp Glu Gln Leu Lys Ser Gly Thr Ala Ser Val Val Cys Leu
            580                 585                 590

Leu Asn Asn Phe Tyr Pro Arg Glu Ala Lys Val Gln Trp Lys Val Asp
        595                 600                 605

Asn Ala Leu Gln Ser Gly Asn Ser Gln Glu Ser Val Thr Glu Gln Asp
        610                 615                 620

Ser Lys Asp Ser Thr Tyr Ser Leu Ser Ser Thr Leu Thr Leu Ser Lys
625                 630                 635                 640

Ala Asp Tyr Glu Lys His Lys Val Tyr Ala Cys Glu Val Thr His Gln
            645                 650                 655

Gly Leu Ser Ser Pro Val Thr Lys Ser Phe Asn Arg Gly Glu Cys
            660                 665                 670

<210> SEQ ID NO 20
<211> LENGTH: 222
<212> TYPE: PRT
<213> ORGANISM: Artificial Sequence
<220> FEATURE:
<223> OTHER INFORMATION: Synthetic

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
            85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
    210                 215                 220

<210> SEQ ID NO 21
<211> LENGTH: 687
```

<212> TYPE: PRT
<213> ORGANISM: Artificial Sequence
<220> FEATURE:
<223> OTHER INFORMATION: Synthetic

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys Gly Gly Ser Gly Gly Gly Ser Gly Gly Ser Gly Gly Gly
450                 455                 460

Ser Glu Val Gln Leu Val Glu Ser Gly Gly Leu Val Gln Pro Gly
465                 470                 475                 480

Gly Ser Leu Arg Leu Ser Cys Ala Ala Ser Gly Tyr Thr Phe Thr Ser
            485                 490                 495

Tyr Trp Leu His Trp Val Arg Gln Ala Pro Gly Lys Gly Leu Glu Trp
        500                 505                 510

Val Gly Met Ile Asp Pro Ser Asn Ser Asp Thr Arg Phe Asn Pro Asn
        515                 520                 525

Phe Lys Asp Arg Phe Thr Ile Ser Ala Asp Thr Ser Lys Asn Thr Ala
530                 535                 540

Tyr Leu Gln Met Asn Ser Leu Arg Ala Glu Asp Thr Ala Val Tyr Tyr
545                 550                 555                 560

Cys Ala Thr Tyr Arg Ser Tyr Val Thr Pro Leu Asp Tyr Trp Gly Gln
            565                 570                 575

Gly Thr Leu Val Thr Val Ser Ser Ala Ser Thr Lys Gly Pro Ser Val
        580                 585                 590

Phe Pro Leu Ala Pro Ser Ser Lys Ser Thr Ser Gly Gly Thr Ala Ala
            595                 600                 605

Leu Gly Cys Leu Val Lys Asp Tyr Phe Pro Glu Pro Val Thr Val Ser
    610                 615                 620

Trp Asn Ser Gly Ala Leu Thr Ser Gly Val His Thr Phe Pro Ala Val
625                 630                 635                 640

Leu Gln Ser Ser Gly Leu Tyr Ser Leu Ser Ser Val Val Thr Val Pro
            645                 650                 655

Ser Ser Ser Leu Gly Thr Gln Thr Tyr Ile Cys Asn Val Asn His Lys
        660                 665                 670

Pro Ser Asn Thr Lys Val Asp Lys Arg Val Glu Pro Lys Ser Cys
    675                 680                 685

<210> SEQ ID NO 22
<211> LENGTH: 220
<212> TYPE: PRT
<213> ORGANISM: Artificial Sequence
<220> FEATURE:
<223> OTHER INFORMATION: Synthetic

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60
```

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 23
<211> LENGTH: 683
<212> TYPE: PRT
<213> ORGANISM: Artificial Sequence
<220> FEATURE:
<223> OTHER INFORMATION: Synthetic

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

-continued

Ser Pro Val Thr Lys Ser Phe Asn Arg Gly Glu Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
    435                 440                 445

Gly Gly Ser Gly Gly Gly Ser Gly Gly Gly Ser Gly Gly Gly Ser Asp
450                 455                 460

Ile Gln Met Thr Gln Ser Pro Ser Ser Leu Ser Ala Ser Val Gly Asp
465                 470                 475                 480

Arg Val Thr Ile Thr Cys Lys Ser Ser Gln Ser Leu Leu Tyr Thr Ser
                485                 490                 495

Ser Gln Lys Asn Tyr Leu Ala Trp Tyr Gln Gln Lys Pro Gly Lys Ala
                500                 505                 510

Pro Lys Leu Leu Ile Tyr Trp Ala Ser Thr Arg Glu Ser Gly Val Pro
            515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Tyr Cys Gln Gln Tyr
545                 550                 555                 560

Tyr Ala Tyr Pro Trp Thr Phe Gly Gln Gly Thr Lys Val Glu Ile Lys
                565                 570                 575

Arg Thr Val Ala Ala Pro Ser Val Phe Ile Phe Pro Pro Ser Asp Glu
            580                 585                 590

Gln Leu Lys Ser Gly Thr Ala Ser Val Val Cys Leu Leu Asn Asn Phe
    595                 600                 605

Tyr Pro Arg Glu Ala Lys Val Gln Trp Lys Val Asp Asn Ala Leu Gln
610                 615                 620

Ser Gly Asn Ser Gln Glu Ser Val Thr Glu Gln Asp Ser Lys Asp Ser 625                 630                 635                 640
Thr Tyr Ser Leu Ser Ser Thr Leu Thr Leu Ser Lys Ala Asp Tyr Glu
                    645                 650                 655
Lys His Lys Val Tyr Ala Cys Glu Val Thr His Gln Gly Leu Ser Ser
                660                 665                 670
Pro Val Thr Lys Ser Phe Asn Arg Gly Glu Cys
            675                 680

<210> SEQ ID NO 24
<211> LENGTH: 222
<212> TYPE: PRT
<213> ORGANISM: Artificial Sequence
<220> FEATURE:
<223> OTHER INFORMATION: Synthetic

<400> SEQUENCE: 24

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Ser Tyr
            20                  25                  30
Trp Leu His Trp Val Arg Gln Ala Pro Gly Lys Gly Leu Glu Trp Val
        35                  40                  45
Gly Met Ile Asp Pro Ser Asn Ser Asp Thr Arg Phe Asn Pro Asn Phe
    50                  55                  60
Lys Asp Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Thr Tyr Arg Ser Tyr Val Thr Pro Leu Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys
    210                 215                 220

<210> SEQ ID NO 25
<211> LENGTH: 120
<212> TYPE: PRT
<213> ORGANISM: Artificial Sequence
<220> FEATURE:
<223> OTHER INFORMATION: Synthetic

<400> SEQUENCE: 25

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
65                   70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
65                   70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 27
<211> LENGTH: 119
<212> TYPE: PRT
<213> ORGANISM: Artificial Sequence
<220> FEATURE:
<223> OTHER INFORMATION: Synthetic

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
65                   70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 29
<211> LENGTH: 119
<212> TYPE: PRT
<213> ORGANISM: Artificial Sequence
<220> FEATURE:
<223> OTHER INFORMATION: Synthetic

<400> SEQUENCE: 29

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asp Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 30
<211> LENGTH: 107
<212> TYPE: PRT
<213> ORGANISM: Artificial Sequence
<220> FEATURE:
<223> OTHER INFORMATION: Synthetic

<400> SEQUENCE: 30

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
            85                  90                  95

Thr Phe Gly Ala Gly Thr Lys Leu Glu Leu Lys
            100                 105

<210> SEQ ID NO 31
<211> LENGTH: 119
<212> TYPE: PRT
<213> ORGANISM: Artificial Sequence
<220> FEATURE:
<223> OTHER INFORMATION: Synthetic

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
            85                  90                  95

Cys Val Arg Asp Arg Val Thr Gly Ala Phe Asp Ile Trp Gly Gln Gly
            100                 105                 110

Thr Met Val Thr Val Ser Ser
        115

<210> SEQ ID NO 32
<211> LENGTH: 107
<212> TYPE: PRT
<213> ORGANISM: Artificial Sequence
<220> FEATURE:
<223> OTHER INFORMATION: Synthetic

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 33
<211> LENGTH: 119
<212> TYPE: PRT
<213> ORGANISM: Artificial Sequence
<220> FEATURE:
<223> OTHER INFORMATION: Synthetic

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser
        115

<210> SEQ ID NO 34
<211> LENGTH: 113
<212> TYPE: PRT
<213> ORGANISM: Artificial Sequence
<220> FEATURE:
<223> OTHER INFORMATION: Synthetic

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys

<210> SEQ ID NO 35
<211> LENGTH: 7
<212> TYPE: PRT
<213> ORGANISM: Artificial Sequence

```
<220> FEATURE:
<223> OTHER INFORMATION: Synthetic

<400> SEQUENCE: 35

Gly Phe Asn Ile Lys Asp Thr
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Tyr Pro Thr Asn Gly Tyr
1               5

<210> SEQ ID NO 37
<211> LENGTH: 11
<212> TYPE: PRT
<213> ORGANISM: Artificial Sequence
<220> FEATURE:
<223> OTHER INFORMATION: Synthetic

<400> SEQUENCE: 37

Trp Gly Gly Asp Gly Phe Tyr Ala Met Asp Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

Arg Ala Ser Gln Asp Val Asn Thr Ala Val Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic

<400> SEQUENCE: 39

Ser Ala Ser Phe Leu Tyr Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Gln Gln His Tyr Thr Thr Pro Pro Thr
1               5

<210> SEQ ID NO 41
<211> LENGTH: 7
<212> TYPE: PRT
<213> ORGANISM: Artificial Sequence
<220> FEATURE:
```

<223> OTHER INFORMATION: Synthetic

<400> SEQUENCE: 41

Gly Phe Thr Phe Thr Asp Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic

<400> SEQUENCE: 42

Asn Pro Asn Ser Gly Gly
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic

<400> SEQUENCE: 43

Asn Leu Gly Pro Ser Phe Tyr Phe Asp Tyr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Lys Ala Ser Gln Asp Val Ser Ile Gly Val Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic

<400> SEQUENCE: 45

Ser Ala Ser Tyr Arg Tyr Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

Gln Gln Tyr Tyr Ile Tyr Pro Tyr Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Gly Phe Ser Leu Thr Asn Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic

<400> SEQUENCE: 48

Trp Ser Gly Gly Asn
1               5

<210> SEQ ID NO 49
<211> LENGTH: 11
<212> TYPE: PRT
<213> ORGANISM: Artificial Sequence
<220> FEATURE:
<223> OTHER INFORMATION: Synthetic

<400> SEQUENCE: 49

Ala Leu Thr Tyr Tyr Asp Tyr Glu Phe Ala Tyr
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic

<400> SEQUENCE: 50

Arg Ala Ser Gln Ser Ile Gly Thr Asn Ile His
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic

<400> SEQUENCE: 51

Tyr Ala Ser Glu Ser Ile Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Gln Gln Asn Asn Asn Trp Pro Thr Thr
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic

```
<400> SEQUENCE: 53

Gly Gly Ser Val Ser Ser Gly Asp Tyr
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic

<400> SEQUENCE: 54

Tyr Tyr Ser Gly Asn
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Asp Arg Val Thr Gly Ala Phe Asp Ile
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Gln Ala Ser Gln Asp Ile Ser Asn Tyr Leu Asn
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic

<400> SEQUENCE: 57

Asp Ala Ser Asn Leu Glu Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic

<400> SEQUENCE: 58

Gln His Phe Asp His Leu Pro Leu Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic

<400> SEQUENCE: 59
```

```
Gly Tyr Thr Phe Thr Ser Tyr
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Asp Pro Ser Asn Ser Asp
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic

<400> SEQUENCE: 61

Tyr Arg Ser Tyr Val Thr Pro Leu Asp Tyr
1               5                   10

<210> SEQ ID NO 62
<211> LENGTH: 17
<212> TYPE: PRT
<213> ORGANISM: Artificial Sequence
<220> FEATURE:
<223> OTHER INFORMATION: Synthetic

<400> SEQUENCE: 62

Lys Ser Ser Gln Ser Leu Leu Tyr Thr Ser Ser Gln Lys Asn Tyr Leu
1               5                   10                  15

Ala

<210> SEQ ID NO 63
<211> LENGTH: 7
<212> TYPE: PRT
<213> ORGANISM: Artificial Sequence
<220> FEATURE:
<223> OTHER INFORMATION: Synthetic

<400> SEQUENCE: 63

Trp Ala Ser Thr Arg Glu Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Tyr Ala Tyr Pro Trp Thr
1               5
```

US 11,951,173 B2

TETRAVALENT ANTIBODY-DRUG CONJUGATES AND USE THEREOF

CROSS REFERENCE TO RELATED APPLICATION

This is a continuation of U.S. Nonprovisional application Ser. No. 16/862,042, filed Apr. 29, 2020, which claims priority to U.S. Provisional Application No. 63/008,726, filed Apr. 11, 2020, the disclosure of each of which is incorporated by reference herein in its entirety.

INCORPORATION OF SEQUENCE LISTING

This application includes a Sequence Listing which is being submitted in ASCII format via EFS-Web, named "BLISS001US_ST25.txt," which is 108 KB in size and created on Apr. 27, 2020. The contents of the Sequence Listing are incorporated herein by reference in their entirety.

BACKGROUND

Antibodies are key immune molecules acting against foreign pathogens. The development of monoclonal antibody (mAb) technology resulted in widespread use of monoclonal antibodies in research, diagnosis and treatment of diseases. The therapeutic use of first-generation mAb (mostly monospecific, bivalent mAb) achieved success in the treatment of a variety of diseases, including cancer, autoimmune, and infectious diseases. However, many diseases, such as solid tumors, have been shown to be quite resistant to antibody-based therapies.

In order to increase potency, improve the safety profile and acquire non-natural properties of mAb, new formats of mAb with modified, multivalent properties have been developed. For example, novel trivalent and tetravalent antibodies have been developed to maximize tumor targeting capabilities through enhanced biodistribution and functional affinity. For example, tetravalent antibodies have been generated for use in cancer immunotherapy, where two binding portions can react with target molecules on the cancer cell surface, while two other binding portions react with cytotoxic T cells or natural killer (NK) cells.

Antibody Drug Conjugates (ADCs) are mAbs chemically linked to active drugs, and therefore, have both the specific targeting of mAbs and the cancer-killing ability of cytotoxic drugs. The ability to select specific mAbs-drug combination and advances in the linking the mAbs and drugs provides new possibilities to target cancers while minimizing exposure of healthy tissue. By 2019, a total of seven ADCs have been approved by the FDA, including: ado-trastuzumab emtansine (Kadcyla™), brentuximab vedotin (Adcetris™), inotuzumab ozogamicin (Besponsa™), gemtuzumab ozogamicin (Mylotarg™), polatuzumab vedotin-piiq (Polivy™) Enfortumab vedotin (Padcev™), and Trastuzumab deruxtecan (Enhertu™). All of them involve conjugation of a cytotoxic drug with a bivalent mAb. In addition to the seven ADC drugs that have been approved for marketing, a large number of ADCs are currently under clinical development.

HER2 (Human Epidermal Growth Factor Receptor 2) also known as Neu, ErbB-2, CD340 or p185, is a member of the epidermal growth factor receptor (EGFR/ErbB) family encoded by the ERBB2 gene. An acquired somatic alteration of this gene resulting in amplification and overexpression occurs in approximately 20-25%, 23-80%, 10-30%, and 20% of human breast, bladder, gastric, and lung cancers, respectively. Amplification and overexpression result in an increase in the proliferative stimuli associated with HER2. This increase in proliferative stimuli results in increased tumor growth. Therefore, enhanced or constitutive HER2 activity was believed to be the driving force of malignances in HER2-expressing human tumor cells. Trastuzumab and Pertuzumab, HER2-targeting monoclonal antibodies, were developed by Roche that hound HER2 and inhibited the tyrosine kinase signal pathway by preventing the necessary dimerization of HER2 or heterodimerization with other members of the HER family (EGFR, HER3 and HER4), which in turn slowed the growth of HER2 overexpressing (HER2-positive) cancer cells. To further improve the therapeutic benefit of HER2-targeting antibody therapies, Roche launched Trastuzumab emtansine (T-DM1), which combines the anti-tumor activity of Trastuzumab with the anti-microtubule agent DM1.

The epidermal growth factor receptor (EGFR, also known as HER1 or c-erbB-1) is a 170 kDa transmembrane glycoprotein and a member of the tyrosine kinase family of cell surface receptors. EGFR is abnormally activated in many epithelial tumors, including those in non-small cell lung cancer, breast cancer, colorectal cancer, head and neck cancers, and prostate cancer. Abnormal activation of EGFR can arise from overexpression of the receptor, gene amplification, activating mutations, overexpression of receptor ligands, and/or loss of regulators of EGFR activity.

Interruption of EGFR signaling, either by blocking EGFR binding sites on the extracellular domain of the receptor or by inhibiting intracellular tyrosine kinase activity, can prevent the growth of EGFR-expressing tumors and improve the patient's condition. Anti☐EGFR antibodies exert antitumor effects by binding the receptor at the cell surface to interfere with ligand binding, which leads to the inhibition of its downstream signaling pathway. The chimeric monoclonal antibody C225 (or cetuximab), which contains the murine variable region of mAb225 and a human IgG1 constant region, is available for treatment of irinotecan-refractory colon cancer in parts of the world.

The approved naked antibodies (i.e., cetuximab, nimotuzumab, panitumumab, and necitumumab) for EGFR demonstrate their therapeutic utility in malignancies but are often used in combination with chemotherapy drugs to achieve significant clinical efficacy. Due to the suboptimal activities of naked antibodies, antibody-drug conjugates (ADC) as the next generation therapies that may increase the antitumor activity of an antibody. In EGFR☐targeted therapy, there is no commercially approved ADC while several ADCs have entered clinical trials. AVID☐100, which is composed of the maytansinoid attached to an anti☐EGFR antibody, was developed to treat epithelial tumor patients in phase I/II. ABT☐414, which is composed of the monomethyl auristatin F attached to an anti☐EGFRvIII antibody via a cleavable linker, has shown significant efficacy against tumors expressing amplified EGFR and EGFRvIII in phase III (van den Bent et al., 2017). All clinical stage EGFR-targeting ADCs have utilized the conventional bivalent anti-EGFR mAbs as targeting antibodies.

SUMMARY

In one aspect, the present disclosure provides an antibody-drug conjugate (ADC), comprising: a tetravalent monoclonal antibody (or tetrabody) conjugated to a cytotoxic drug by a chemical linker, wherein the monoclonal antibody comprises two long chains and four short chains, wherein each of the long chains comprises a first segment and a second segment, the first segment located proximal to the N-terminus of the long chain, and the second segment located proximal to the C-terminus of the long chain, each of the first segment and second segment paring with one of the short chains to form an antigen-binding fragment domain, therefore forming four antigen-binding fragment domains having specificity toward the same antigen.

In some embodiments of the ADC, the two long chains are identical to each other, and the four short chains are identical to each other. In some embodiments, the two long chains can be different from each other. In some embodiments, the four short chains can be not all identical to each other.

In some embodiments, the first segment and the second segment of at least one, or each, of the long chains have identical sequence. In some other embodiments, the first segment and the second segment of at least one, or each, of the long chains can have different sequences.

In some embodiments of the ADC, each of the long chains comprises a subsequence having the sequence of CH2-CH3 domain of one of a native human IgG1, IgG2, IgG4 antibody isotypes, the subsequence disposed between the first segment and the second segment.

In some embodiments of the ADC, each of the long chains comprises a subsequence disposed between the first segment and the second segment, the subsequence comprises the Fc (or CH2-CH3) domain of a human IgG1 isotype. In some embodiments, such Fc domain can include one or more mutations for desired improvements of Fc domain functions.

In some embodiments of the ADC, at least one, or each of, the short chains comprises the sequence of VL-CL(λ) or VL-CL(κ) of a native human IgG antibody isotype.

In some embodiments of the ADC, at least one, or each, of the short chains comprises the sequence of VH-CH1, where CH1 is of a human IgG antibody isotype. In some of such embodiments, the VH can contain one or more mutations.

In some embodiments of the ADC, at least one of the first segment or the second segment of at least one of the long chains comprises a sequence of VL-CL(κ) of a native human IgG1, IgG2, or IgG4 antibody isotype.

In some embodiments of the ADC, the long chains each comprises a sequence selected from the group consisting of SEQ ID NOs: 3, 5, and 9, and the short chains each comprises a sequence selected from the group consisting of SEQ ID NOs: 4, 6, and 10.

In some embodiments, the first segment and second segment of each of the long chains each comprises a sequence selected from the group consisting of SEQ ID NOs: 25, 26, 27, 28, 29, 30, 31, 32, 33, and 34.

In some embodiments, the first segment and second segment of each of the short chains each comprises a sequence selected from the group consisting of SEQ ID NOs: 25, 26, 27, 28, 29, 30, 31, 32, 33, and 34.

In some embodiments, each of the long chains comprises the sequence of SEQ ID NO:25 and each of the short chains comprises the sequence of SEQ ID NO:26. In some embodiments, each of the long chains comprises the sequence of SEQ ID NO:26 and each of the short chains comprises the sequence of SEQ ID NO:25. In some embodiments, each of the long chains comprises the sequence of SEQ ID NO:27 and each of the short chains comprises the sequence of SEQ ID NO:28. In some embodiments, each of the long chains comprises the sequence of SEQ ID NO:28 and each of the short chains comprises the sequence of SEQ ID NO:27. In some embodiments, each of the long chains comprises the sequence of SEQ ID NO:29 and each of the short chains comprises the sequence of SEQ ID NO:30. In some embodiments, each of the long chains comprises the sequence of SEQ ID NO:30 and each of the short chains comprises the sequence of SEQ ID NO:29. In some embodiments, each of the long chains comprises the sequence of SEQ ID NO:31 and each of the short chains comprises the sequence of SEQ ID NO:32. In some embodiments, each of the long chains comprises the sequence of SEQ ID NO:32 and each of the short chains comprises the sequence of SEQ ID NO:31. In some embodiments, each of the long chains comprises the sequence of SEQ ID NO:33 and each of the short chains comprises the sequence of SEQ ID NO:34. In some embodiments, each of the long chains comprises the sequence of SEQ ID NO:34 and each of the short chains comprises the sequence of SEQ ID NO:34.

In some embodiments of the ADC, each of the short chains comprises a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, and SEQ ID NO:24.

In some embodiments of the ADC, each of the long chains comprises a sequence selected from the group consisting of SEQ ID NO:1, SEQ ID NO:3, SEQ ID NO:5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, and SEQ ID NO:23.

In some embodiments of the ADC, the long chains each comprise a sequence of SEQ ID NO:1 and the short chains each comprise a sequence of SEQ ID NO:2. In some embodiments of the ADC, the long chains each comprise a of SEQ ID NO:3 and the short chains each comprise a sequence of SEQ ID NO:4. In some embodiments of the ADC, the long chains each comprise a sequence of SEQ ID NO:5 and the short chains each comprise a sequence of SEQ ID NO:6. In some embodiments of the ADC, the long chains each comprise a sequence of SEQ ID NO:7 and the short chains each comprise a sequence of SEQ ID NO:8. In some embodiments of the ADC, the long chains each comprise a sequence of SEQ ID NO:9 and the short chains each comprise a sequence of SEQ ID NO:10.

In some embodiments of the ADC, the long chains each comprise a sequence of SEQ ID NO:11 and the short chains each comprise a sequence of SEQ ID NO:12. In some embodiments of the ADC, the long chains each comprise a of SEQ ID NO:13 and the short chains each comprise a sequence of SEQ ID NO:14. In some embodiments of the ADC, the long chains each comprise a sequence of SEQ ID NO:15 and the short chains each comprise a sequence of SEQ ID NO:16. In some embodiments of the ADC, the long chains each comprise a sequence of SEQ ID NO:17 and the short chains each comprise a sequence of SEQ ID NO:18. In some embodiments of the ADC, the long chains each comprise a sequence of SEQ ID NO:19 and the short chains each comprise a sequence of SEQ ID NO:20. In some embodiments of the ADC, the long chains each comprise a sequence of SEQ ID NO:21 and the short chains each comprise a sequence of SEQ ID NO:22. In some embodiments of the ADC, the long chains each comprise a sequence of SEQ ID NO:23 and the short chains each comprise a sequence of SEQ ID NO:24.

In some embodiments, the present disclosure provides an ADC which comprises a monoclonal antibody conjugated to a cytotoxic drug by a chemical linker, wherein the monoclonal antibody comprises two identical long chains and four identical short chains, wherein:

(a) each of the long chains comprises the sequence of SEQ ID NO:1 and each of the short chains comprises the sequence of SEQ ID NO:2; or
(b) each of the long chains comprises the sequence of SEQ ID NO:3 and each of the short chains comprises the sequence of SEQ ID NO:4; or
(c) each of the long chains comprises the sequence of SEQ ID NO:5 and each of the short chains comprises the sequence of SEQ ID NO:6; or
(d) each of the long chains comprises the sequence of SEQ ID NO:7 and each of the short chains comprises the sequence of SEQ ID NO:8; or
(e) each of the long chains comprises the sequence of SEQ ID NO:9 and each of the short chains comprises the sequence of SEQ ID NO:10; or
(f) each of the long chains comprises the sequence of SEQ ID NO:11 and each of the short chains comprises the sequence of SEQ ID NO:12; or
(g) each of the long chains comprises the sequence of SEQ ID NO:13 and each of the short chains comprises the sequence of SEQ ID NO:14; or
(h) each of the long chains comprises the sequence of SEQ ID NO:15 and each of the short chains comprises the sequence of SEQ ID NO:16; or
(i) each of the long chains comprises the sequence of SEQ ID NO:17 and each of the short chains comprises the sequence of SEQ ID NO:18; or
(j) each of the long chains comprises the sequence of SEQ ID NO:19 and each of the short chains comprises the sequence of SEQ ID NO:20; or
(k) each of the long chains comprises the sequence of SEQ ID NO:21 and each of the short chains comprises the sequence of SEQ ID NO:22; or
(l) each of the long chains comprises the sequence of SEQ ID NO:23 and each of the short chains comprises the sequence of SEQ ID NO:24.

In some embodiments of the ADC, the second segment is connected to the remainder of the long chain via a flexible peptide linker comprising an amino sequence of $(G_xS)_y$, where x is a whole number between 1 and 6 inclusive and y is a whole number between 1 and 8 inclusive.

In some embodiments, the antigen is EGFR, and the ADC contains four antigen-binding fragment domains all specifically bind to EGFR. In some embodiments, the antigen is HER2, and the ADC contains four antigen-binding fragment domains all specifically bind to HER2. In some embodiments, the antigen is c-MET, and the ADC contains four antigen-binding fragment domains all specifically bind to c-MET.

In some embodiments of the ADC, the cytotoxic drug is selected from the group consisting of monomethyl auristatin E (MMAE), monomethyl auristatin F (MMAF), auristatin E, auristatin F, maytansine DM1 and DM4, maytansinol, sandramycin, pyrrolobenzodiazepine dimer, anthracyclines, calicheamicin, dolastatin 10, duocarmycin, doxorubicin, thailanstatin A, uncialamycin, amanitins, ricin, diphtheria toxin, eribulin, $^{131}$I, interleukins, tumor necrosis factors, chemokines, and nanoparticles.

In some embodiments of the ADC, the linker is cleavable or non-cleavable, and can be selected from the group consisting of 6-maleimidocaproyl (MC), maleimidopropionyl (MP), valine-citrulline (val-cit), alanine-phenylalanine (ala-phe), p-aminobenzyloxycarbonyl (PAB), N-succinimidyl 4-(2-pyridylthio)valerate (SPP), N-succinimidyl 4-(N-maleimidomethyl)-cyclohexane-1-carboxylate (SMCC), N-succinimidyl (4-iodo-acetyl) aminobenzoate (SIAB), 6-maleimidocaproyl-valine-citrulline-p-aminobenzyloxycarbonyl (MC-vc-PAB), Val-Cit-PABC, N-succinimidyl-4-(2-pyridyldithio)butanoate (SPDB), N-succinimidyl 3-(pyridin-2-yldithio)-propionate (SPDP), Phe-Lys(Fmoc)-PAB, Aloc-D-Ala-Phe-Lys(Aloc)-PAB-PNP, Boc-Phe-(Alloc) Lys-PAB-PNP, and perfluorophenyl 3-(pyridine-2-yldisulfanyl) propanoate.

In some embodiments of the ADC, the drug-linker can be attached to tetravalent antibody through cysteine coupling, amine coupling, terminal coupling, enzymatic coupling, or carbohydrate coupling.

In some embodiments of the ADC, the drug-to-antibody ratio is between 1 and 12 inclusive. In some embodiments, the drug-to-antibody ratio is about 3 or 4.

The present disclosure also provides a pharmaceutically acceptable salt thereof, of the various embodiments of the ADCs as described herein.

In a further aspect, the present disclosure provides a pharmaceutical composition comprising the ADC, or the pharmaceutically acceptable salt thereof, and a pharmaceutically acceptable carrier.

In a further aspect, the present disclosure provides a method of treating a proliferative disease, disorder, or condition, by administering to a subject an effective amount of the pharmaceutical composition described herein. The proliferative disease may be cancers, such as colon cancer, rectal cancer, lung cancer, breast cancer, ovarian cancer, cervical cancer, bladder cancer, esophageal cancer, sarcoma, and head and neck cancer.

BRIEF DESCRIPTION OF THE DRAWINGS

FIGS. 6A-6C show internalization analysis of tetravalent ADCs of some embodiments of the present disclosure and control ADC. 6A: ADC with MMAE payload on EGFR high-expressing MDA-MB-468 cells; 6B: ADC with DM1 payload on MDA-MB-468 cells; 6C: ADC with MMAE payload on EGFR low-expressing NUGC3 cells.

FIGS. 7A-7C show cytotoxicity of tetravalent ADCs of embodiments of the present disclosure and control ADC. 7A: ADC with MMAE payload to EGFR high-expressing MDA-MB-468 cells; 7B: ADC with DM1 payload to MDA-MB-468 cells; 7C: ADC with MMAE payload to EGFR low-expressing NUGC3 cells.

DETAILED DESCRIPTION

Figure 1:
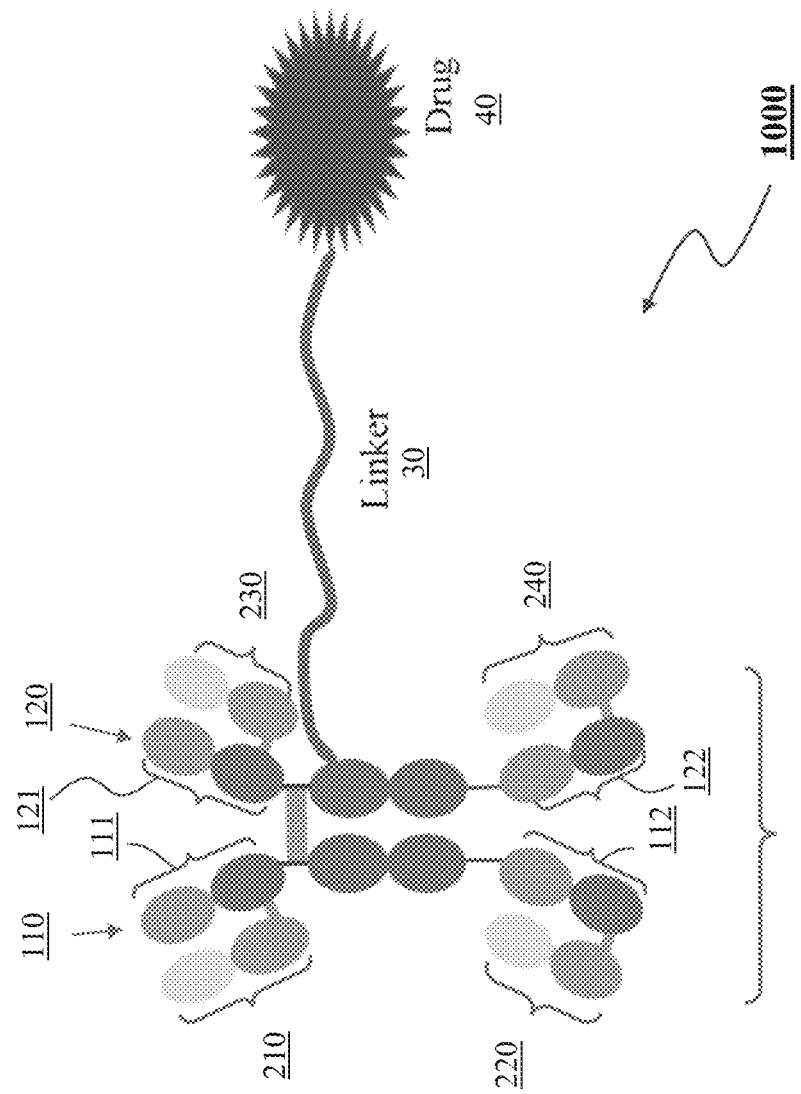
FIG. 1 is a schematic depiction of the structure of a tetravalent ADC in accordance with embodiments of the present disclosure.

In one aspect, and in connection with illustration shown in FIG. 1, the present disclosure provides an antibody-drug conjugate (ADC) 1000, comprising: a tetravalent monoclonal antibody 10 conjugated to a cytotoxic drug 40 by a chemical linker 30, wherein the monoclonal antibody 10 comprises two long chains (110 and 120) and four short chains (210, 220, 230 and 240), wherein each of the long chains comprises an first segment (111, 121) and a second segment (112, 122), the first segment located proximal to the N-terminus of the long chain, and the second segment located proximal to the C-terminus of the long chain, each of the first segment and second segment paring with one of the short chains to form an antigen-binding fragment domain, therefore forming four antigen-binding fragment domains having binding specificity toward a same antigen.

As used herein, an antibody or a portion thereof that "specifically binds" targets (or target antigen, e.g., HER2, HER3, EGFR, CLDN18.2, TROP2, BMCA, CD33, CD22, CD72 or other antigens) can refer to an antibody or a portion thereof that binds to a human target protein to therefore inhibit its associated signaling. Preferably, the antibody binds to a human target protein with "high affinity," namely with a KD of $1 \times 10^{-8}$ M or less, more preferably $5 \times 10^{-9}$ M or less or even more preferably $1 \times 10^{-9}$ M or less.

As used herein, the term "cytotoxic drug" or "cytotoxic agent", as used herein, is meant to refer to any agent or drug known to inhibit the growth and/or replication of, and/or kill cells. As a component of the ADC, it is also referred to as the "payload".

In some embodiments, the construction of a tetravalent monospecific antibody of the present disclosure can be considered as attaching of the intact Fab domain of a precursor antibody to the Fc C-terminal of the same precursor antibody, or to the Fc C-terminal of a different precursor antibody with the same antigen specificity.

Proper arrangement and spacing of the antigen-binding regions of a tetravalent antibody facilitate multivalent engagement of several molecules of the same antigen on cell surface. Ill-designed antibodies could cause hindrance of some binding epitopes. The design of the invention spaces out the four Fab domains, two on each side of the Fc domain, with the ones on C-terminal linked with a flexible GS linker. This arrangement offers suitable flexibility and ranges for each arm (Fab) to reach (bind to) a target antigen, and can minimize the steric hindrance of different Fabs.

The tetravalent antibodies of the present disclosure could engage target through both N-terminal Fabs and C-terminal Fabs simultaneously, and the multivalent engagement could induce more effective internalization of the target-antibody complex. This offers a distinct advantage of the tetravalent ADC over the traditional ADC.

Multivalent antibodies with scFv fused to the C-terminal of Fc have been reported. The major challenge of such design is the reduced affinities when Fab structure is converted to scFv. Most Mab sequences when converted to scFv became either unstable or with reduced affinity. In contrast, Fab with intact VH-CH1 and VL-CL is generally stable and retains its affinity.

Tetravalent antibody-drug conjugate of the present disclosure takes advantage of the enhanced internalization capability of ADC-target complex through multivalent engagement of antigens on cancer cells that potentially improves the delivery of cytotoxic drugs into target expressing tumor cells.

In some embodiments of the ADC, the two long chains are identical to each other, and the four short chains are identical to each other. In some embodiments, the two long chains can be different from each other. In some embodiments, the four short chains can be not all identical to each other.

In some embodiments of the ADC, the first segment and the second segment of at least one, or each, of the long chains have identical sequence. In some other embodiments, the first segment and the second segment of at least one, or each, of the long chains can have different sequences.

In some embodiments of the ADC, each of the long chains comprises a subsequence having the sequence of CH2-CH3 domain of one of a native human IgG1, IgG2, IgG4 antibody isotypes, the subsequence disposed between the first segment and the second segment.

In some embodiments of the ADC, each of the long chains comprises a subsequence disposed between the first segment and the second segment, the subsequence comprises the CH2-CH3 (or Fc) domain of a human IgG isotype, where such Fc domain can contain one or more mutations for desired improvement of Fc functions.

In some embodiments of the ADC, at least one, or each of, the short chains comprise the sequence of VL-CL(λ) or VL-CL(κ) of a native human IgG antibody isotype.

In some embodiments of the ADC, at least one, or each, of the short chains comprises the sequence of VH-CH1, where CH1 is of a human IgG antibody isotype. The VH portion of the sequence can include one or more mutations.

In some embodiments of the ADC, at least one of the first segment or the second segment of at least one of the long chains comprises a sequence of VL-CL(κ) of a native human IgG1, IgG2, or IgG4 antibody isotype.

In some embodiments of the ADC, the long chains each comprises a sequence selected from the group consisting of SEQ ID NOs: 3, 5, and 9, and the short chains each comprises a sequence selected from the group consisting of SEQ ID NOs: 4, 6, and 10.

In some embodiments of the ADC, the first segment and second segment of each of the long chains each comprises a sequence selected from the group consisting of SEQ ID NOs: 25, 26, 27, 28, 29, 30, 31, 32, 33, and 34.

In some embodiments of the ADC, the first segment and second segment of each of the long chains each comprises a sequence selected from the group consisting of:

(1) an antigen-binding sequence comprising (1a) CDR1 comprising SEQ ID NO:35, (1b) CDR2 comprising SEQ ID NO:36, and (1c) CDR3 comprising SEQ ID NO:37;

(2) an antigen-binding sequence comprising (2a) CDR1 comprising SEQ ID NO:38, (2b) CDR2 comprising SEQ ID NO:39, and (2c) CDR3 comprising SEQ ID NO:40;

(3) an antigen-binding sequence comprising (3a) CDR1 comprising SEQ ID NO:41, (3b) CDR2 comprising SEQ ID NO:42, and (3c) CDR3 comprising SEQ ID NO:43;

(4) an antigen-binding sequence comprising (4a) CDR1 comprising SEQ ID NO:44, (4b) CDR2 comprising SEQ ID NO:45, and (4c) CDR3 comprising SEQ ID NO:46;

(5) an antigen-binding sequence comprising (5a) CDR1 comprising SEQ ID NO:47, (5b) CDR2 comprising SEQ ID NO:48, and (5c) CDR3 comprising SEQ ID NO:49;

(6) an antigen-binding sequence comprising (6a) CDR1 comprising SEQ ID NO:50, (6b) CDR2 comprising SEQ ID NO:51, and (6c) CDR3 comprising SEQ ID NO:52;

(7) an antigen-binding sequence comprising (7a) CDR1 comprising SEQ ID NO:53, (7b) CDR2 comprising SEQ ID NO:54, and (7c) CDR3 comprising SEQ ID NO:55;

(8) an antigen-binding sequence comprising (8a) CDR1 comprising SEQ ID NO:56, (8b) CDR2 comprising SEQ ID NO:57, and (8c) CDR3 comprising SEQ ID NO:58;
(9) an antigen-binding sequence comprising (9a) CDR1 comprising SEQ ID NO:59, (9b) CDR2 comprising SEQ ID NO:60, and (9c) CDR3 comprising SEQ ID NO:61; and
(10) an antigen-binding sequence comprising (10a) CDR1 comprising SEQ ID NO:62, (10b) CDR2 comprising SEQ ID NO:63; and (10c) CDR3 comprising SEQ ID NO:64.

In some embodiments of the ADC, the first segment and second segment of each of the short chains each comprises a sequence selected from the group consisting of SEQ ID NOs: 25, 26, 27, 28, 29, 30, 31, 32, 33, and 34.

In some embodiments of the ADC, the first segment and second segment of each of the short chains each comprises a sequence selected from the group consisting of:
(1) an antigen-binding sequence comprising (1a) CDR1 comprising SEQ ID NO:35, (1b) CDR2 comprising SEQ ID NO:36, and (1c) CDR3 comprising SEQ ID NO:37;
(2) an antigen-binding sequence comprising (2a) CDR1 comprising SEQ ID NO:38, (2b) CDR2 comprising SEQ ID NO:39, and (2c) CDR3 comprising SEQ ID NO:40;
(3) an antigen-binding sequence comprising (3a) CDR1 comprising SEQ ID NO:41, (3b) CDR2 comprising SEQ ID NO:42, and (3c) CDR3 comprising SEQ ID NO:43;
(4) an antigen-binding sequence comprising (4a) CDR1 comprising SEQ ID NO:44, (4b) CDR2 comprising SEQ ID NO:45, and (4c) CDR3 comprising SEQ ID NO:46;
(5) an antigen-binding sequence comprising (5a) CDR1 comprising SEQ ID NO:47, (5b) CDR2 comprising SEQ ID NO:48, and (5c) CDR3 comprising SEQ ID NO:49;
(6) an antigen-binding sequence comprising (6a) CDR1 comprising SEQ ID NO:50, (6b) CDR2 comprising SEQ ID NO:51, and (6c) CDR3 comprising SEQ ID NO:52;
(7) an antigen-binding sequence comprising (7a) CDR1 comprising SEQ ID NO:53, (7b) CDR2 comprising SEQ ID NO:54, and (7c) CDR3 comprising SEQ ID NO:55;
(8) an antigen-binding sequence comprising (8a) CDR1 comprising SEQ ID NO:56, (8b) CDR2 comprising SEQ ID NO:57, and (8c) CDR3 comprising SEQ ID NO:58;
(9) an antigen-binding sequence comprising (9a) CDR1 comprising SEQ ID NO:59, (9b) CDR2 comprising SEQ ID NO:60, and (9c) CDR3 comprising SEQ ID NO:61; and
(10) an antigen-binding sequence comprising (10a) CDR1 comprising SEQ ID NO:62, (10b) CDR2 comprising SEQ ID NO:63, and (10c) CDR3 comprising SEQ ID NO:64.

In some embodiments of the ADC, each of the long chains comprises the sequence of SEQ ID NO:25 and each of the short chains comprises the sequence of SEQ ID NO:26. In some embodiments, each of the long chains comprises the sequence of SEQ ID NO:26 and each of the short chains comprises the sequence of SEQ ID NO:25. In some embodiments, each of the long chains comprises the sequence of SEQ ID NO:27 and each of the short chains comprises the sequence of SEQ ID NO:28. In some embodiments, each of the long chains comprises the sequence of SEQ ID NO:28 and each of the short chains comprises the sequence of SEQ ID NO:27. In some embodiments, each of the long chains comprises the sequence of SEQ ID NO:29 and each of the short chains comprises the sequence of SEQ ID NO:30. In some embodiments, each of the long chains comprises the sequence of SEQ ID NO:30 and each of the short chains comprises the sequence of SEQ ID NO:29. In some embodiments, each of the long chains comprises the sequence of SEQ ID NO:31 and each of the short chains comprises the sequence of SEQ ID NO:32. In some embodiments, each of the long chains comprises the sequence of SEQ ID NO:32 and each of the short chains comprises the sequence of SEQ ID NO:31. In some embodiments, each of the long chains comprises the sequence of SEQ ID NO:33 and each of the short chains comprises the sequence of SEQ ID NO:34. In some embodiments, each of the long chains comprises the sequence of SEQ ID NO:34 and each of the short chains comprises the sequence of SEQ ID NO:33.

In some embodiments of the ADC, each of the long chains comprises an antigen-binding sequence comprising three CDR regions respectively comprising the sequences of SEQ ID NO:35, SEQ ID NO:36 and SEQ ID NO:37, and each of the short chains comprises an antigen-binding sequence comprising three CDR regions respectively comprising the sequences of SEQ ID NO:38, SEQ ID NO:39 and SEQ ID NO:40. In some embodiments of the ADC, each of the short chains comprises an antigen-binding sequence comprising three CDR regions respectively comprising the sequences of SEQ ID NO:35, SEQ ID NO:36 and SEQ ID NO:37, and each of the long chains comprises an antigen-binding sequence comprising three CDR regions respectively comprising the sequences of SEQ ID NO:38, SEQ ID NO:39 and SEQ ID NO:40.

In some embodiments of the ADC, each of the long chains comprises an antigen-binding sequence comprising three CDR regions respectively comprising the sequences of SEQ ID NO:41, SEQ ID NO:42 and SEQ ID NO:43, and each of the short chains comprises an antigen-binding sequence comprising three CDR regions respectively comprising the sequences of SEQ ID NO:44, SEQ ID NO:45 and SEQ ID NO:46. In some embodiments of the ADC, each of the short chains comprises an antigen-binding sequence comprising three CDR regions respectively comprising the sequences of SEQ ID NO:41, SEQ ID NO:42 and SEQ ID NO:43, and each of the long chains comprises an antigen-binding sequence comprising three CDR regions respectively comprising the sequences of SEQ ID NO:44, SEQ ID NO:45 and SEQ ID NO:46.

In some embodiments of the ADC, each of the long chains comprises an antigen-binding sequence comprising three CDR regions respectively comprising the sequences of SEQ ID NO:47, SEQ ID NO:48 and SEQ ID NO:49, and each of the short chains comprises an antigen-binding sequence comprising three CDR regions respectively comprising the sequences of SEQ ID NO:50, SEQ ID NO:51 and SEQ ID NO:52. In some embodiments of the ADC, each of the short chains comprises an antigen-binding sequence comprising three CDR regions respectively comprising the sequences of SEQ ID NO:47, SEQ ID NO:48 and SEQ ID NO:49, and each of the long chains comprises an antigen-binding sequence comprising three CDR regions respectively comprising the sequences of SEQ ID NO:50, SEQ ID NO:51 and SEQ ID NO:52.

In some embodiments of the ADC, each of the long chains comprises an antigen-binding sequence comprising three CDR regions respectively comprising the sequences of SEQ ID NO:53, SEQ ID NO:54 and SEQ ID NO:55, and each of the short chains comprises an antigen-binding sequence comprising three CDR regions respectively comprising the sequences of SEQ ID NO:56, SEQ ID NO:57 and SEQ ID NO:58. In some embodiments of the ADC, each of the short chains comprises an antigen-binding sequence comprising three CDR regions respectively comprising the sequences of SEQ ID NO:53, SEQ ID NO:54 and SEQ ID NO:55, and each of the long chains comprises an antigen-binding sequence comprising three CDR regions respectively comprising the sequences of SEQ ID NO:56, SEQ ID NO:57 and SEQ ID NO:58.

In some embodiments of the ADC, each of the long chains comprises an antigen-binding sequence comprising three CDR regions respectively comprising the sequences of SEQ ID NO:59, SEQ ID NO:60 and SEQ ID NO:61, and each of the short chains comprises an antigen-binding sequence comprising three CDR regions respectively comprising the sequences of SEQ ID NO:62, SEQ ID NO:63 and SEQ ID NO:64. In some embodiments of the ADC, each of the short chains comprises an antigen-binding sequence comprising three CDR regions respectively comprising the sequences of SEQ ID NO:59, SEQ ID NO:60 and SEQ ID NO:61, and each of the long chains comprises an antigen-binding sequence comprising three CDR regions respectively comprising the sequences of SEQ ID NO:62, SEQ ID NO:63 and SEQ ID NO:64.

In some embodiments of the ADC, each of the short chains comprises a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, and SEQ ID NO:24.

In some embodiments of the ADC, each of the long chains comprises a sequence selected from the group consisting of SEQ ID NO:1, SEQ ID NO:3, SEQ ID NO:5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, and SEQ ID NO:23.

In some embodiments of the ADC, the long chains each comprise a sequence of SEQ ID NO:1 and the short chains each comprise a sequence of SEQ ID NO:2. In some embodiments of the ADC, the long chains each comprise a of SEQ ID NO:3 and the short chains each comprise a sequence of SEQ ID NO:4. In some embodiments of the ADC, the long chains each comprise a sequence of SEQ ID NO:5 and the short chains each comprise a sequence of SEQ ID NO:6. In some embodiments of the ADC, the long chains each comprise a sequence of SEQ ID NO:7 and the short chains each comprise a sequence of SEQ ID NO:8. In some embodiments of the ADC, the long chains each comprise a sequence of SEQ ID NO:9 and the short chains each comprise a sequence of SEQ ID NO:10.

In some embodiments of the ADC, the long chains each comprise a sequence of SEQ ID NO:11 and the short chains each comprise a sequence of SEQ ID NO:12. In some embodiments of the ADC, the long chains each comprise a of SEQ ID NO:13 and the short chains each comprise a sequence of SEQ ID NO:14. In some embodiments of the ADC, the long chains each comprise a sequence of SEQ ID NO:15 and the short chains each comprise a sequence of SEQ ID NO:16. In some embodiments of the ADC, the long chains each comprise a sequence of SEQ ID NO:17 and the short chains each comprise a sequence of SEQ ID NO:18. In some embodiments of the ADC, the long chains each comprise a sequence of SEQ ID NO:19 and the short chains each comprise a sequence of SEQ ID NO:20. In some embodiments of the ADC, the long chains each comprise a sequence of SEQ ID NO:21 and the short chains each comprise a sequence of SEQ ID NO:22. In some embodiments of the ADC, the long chains each comprise a sequence of SEQ ID NO:23 and the short chains each comprise a sequence of SEQ ID NO:24.

In some embodiments, the present disclosure provides an ADC which comprises a monoclonal antibody conjugated to a cytotoxic drug by a chemical linker, wherein the monoclonal antibody comprises two identical long chains and four identical short chains, wherein:

(a) each of the long chains comprises the sequence of SEQ ID NO:1 and each of the short chains comprises the sequence of SEQ ID NO:2; or (b) each of the long chains comprises the sequence of SEQ ID NO:3 and each of the short chains comprises the sequence of SEQ ID NO:4; or (c) each of the long chains comprises the sequence of SEQ ID NO:5 and each of the short chains comprises the sequence of SEQ ID NO:6; or (d) each of the long chains comprises the sequence of SEQ ID NO:7 and each of the short chains comprises the sequence of SEQ ID NO:8; or (e) each of the long chains comprises the sequence of SEQ ID NO:9 and each of the short chains comprises the sequence of SEQ ID NO:10; or (f) each of the long chains comprises the sequence of SEQ ID NO:11 and each of the short chains comprises the sequence of SEQ ID NO:12; or (g) each of the long chains comprises the sequence of SEQ ID NO:13 and each of the short chains comprises the sequence of SEQ ID NO:14; or (h) each of the long chains comprises the sequence of SEQ ID NO:15 and each of the short chains comprises the sequence of SEQ ID NO:16; or (i) each of the long chains comprises the sequence of SEQ ID NO:17 and each of the short chains comprises the sequence of SEQ ID NO:18; or (j) each of the long chains comprises the sequence of SEQ ID NO:19 and each of the short chains comprises the sequence of SEQ ID NO:20; or (k) each of the long chains comprises the sequence of SEQ ID NO:21 and each of the short chains comprises the sequence of SEQ ID NO:22; or (l) each of the long chains comprises the sequence of SEQ ID NO:23 and each of the short chains comprises the sequence of SEQ ID NO:24.

In some embodiments of the ADC, the second segment is connected to the remainder of the long chain via a flexible peptide linker comprising an amino sequence of $(G_xS)_y$, where x is a whole number between 1 and 6 inclusive and y is a whole number between 1 and 8 inclusive.

In some embodiments, the antigen is HER2, EGFR, cMet or other antigens, and the ADC contains four antigen-binding fragment domains all specifically bind to these antigens.

In some embodiments of the ADC, the cytotoxic drug is selected from the group consisting of monomethyl auristatin E (MMAE), monomethyl auristatin F (MMAF), auristatin E, auristatin F, maytansine DM1 and DM4, maytansinol, sandramycin, pyrrolobenzodiazepine dimer, anthracyclines, calicheamicin, dolastatin 10, duocarmycin, doxorubicin, thailanstatin A, uncialamycin, amanitins, ricin, diphtheria toxin, eribulin, $^{131}$I, interleukins, tumor necrosis factors, chemokines, and nanoparticles. In one embodiment, the cytotoxic drug is MMAE. In one embodiment, the cytotoxic drug is MMAF. In one embodiment, the cytotoxic drug is DM1. In one embodiment, the cytotoxic drug is DM4.

The chemical linker linking the antibody portion and the cytotoxic drug can be cleavable or non-cleavable. In some embodiments, the linker comprises a PEGn where n is between 1 and 20 (i.e., having 1 to 20 repeat units ($CH_2CH_2O$)). In some embodiments, the chemical linker further comprises a peptide linker connected to the PEGn spacer. In some embodiments, the chemical linker comprises a peptide linker but does not comprise the PEGn spacer. The peptide linker can be selected from the group consisting of 6-maleimidocaproyl (MC), maleimidopropionyl (MP), valine-citrulline (val-cit), alanine-phenylalanine (ala-phe), p-aminobenzyloxycarbonyl (PAB), N-succinimidyl 4-(2-pyridylthio)valerate (SPP), N-succinimidyl 4-(N-maleimidomethyl)-cyclohexane-1-carboxylate (SMCC), N-succinimidyl (4-iodo-acetyl) aminobenzoate (STAB), 6-maleimidocaproyl-val-cit-p-aminobenzyloxycarbonyl (MC-vc-PAB), val-cit-PABC, N-succinimidyl-4-(2-pyridyl-dithio)butanoate (SPDB), N-succinimidyl 3-(pyridin-2-yldithio)-propionate (SPDP), Phe-Lys(Fmoc)-PAB, Aloc-D-Ala-Phe-Lys(Aloc)-PAB-PNP, Boc-Phe-(Alloc)Lys-PAB-PNP, and perfluorophenyl 3-(pyridine-2-yldisulfanyl) propanoate.

In some embodiments of the ADC, the drug-linker can be attached to tetrabody through cysteine coupling, amine coupling, terminal coupling, enzymatic coupling, or carbohydrate coupling.

In some embodiments of the ADC, the drug-to-antibody ratio is between 1 and 12 inclusive. In some embodiments, the drug-to-antibody ratio is about 3 or 4.

The present disclosure also provides a pharmaceutically acceptable salt thereof, of the various embodiments of the ADCs as described herein.

In a further aspect, the present disclosure provides a pharmaceutical composition comprising the ADC, or the pharmaceutically acceptable salt thereof, and a pharmaceutically acceptable carrier.

In a further aspect, the present disclosure provides a method of treating a proliferative disease, disorder, or condition, by administering to a subject an effective amount of the pharmaceutical composition described herein. The proliferative disease may be cancers, such as colon cancer, rectal cancer, lung cancer, breast cancer, ovarian cancer, cervical cancer, bladder cancer, esophageal cancer, sarcoma, and head and neck cancer. The present disclosure also provides a method of treating an EGRF, HER2, or c-MET associated disease, disorder or condition, such as a proliferative disease, disorder or condition, e.g., cancer.

In another aspect, the present disclosure provides nucleic acid molecules encoding the antibodies, or antigen-binding portions, of the invention. Recombinant expression vectors which include nucleic acids encoding antibodies of the invention, and host cells transfected with such vectors, are also encompassed by the invention, as are methods of making the antibodies of the invention by culturing such host cells, e.g., an expression vector comprising a nucleotide sequence encoding the variable and constant regions of the heavy and light chains of antibody 2F8 produced by the hybridoma.

The present disclosure also provides mammalian cells capable of producing the monoclonal antibodies of the invention that specifically bind to the intended targets. In one embodiment, the hybridoma includes a B cell obtained from a transgenic non-human animal, e.g., a transgenic mouse having a genome comprising a human heavy chain transgene and a human light chain transgene encoding all or a portion of an antibody of the invention, fused to an immortalized cell.

The term "about" as used herein with reference to a certain given value or quantity herein means a range of up to 25% deviation from (greater or smaller than) the given value.

As used herein, the term "cancer" is intended to encompass both non-metastatic cancer and metastatic cancer. In this context, treating cancer involves treatment of both primary tumors and tumor metastases.

As used herein, "treatment" refers to clinical intervention that attempts to alter the natural course of a treated individual, which can include the prevention of recurrence or relapse of disease, the alleviation of symptoms, the weakening of any direct or indirect pathological consequences of disease, the prevention of metastasis, the reduction of disease progression rate, the improvement or alleviation of disease status, and the elimination or improvement of prognosis.

In the present disclosure, "subject" refers to mammal, such as cattle, cats, dogs, and horses, primates, mice and rats. In certain embodiments, the mammal refers to a human.

In the present disclosure, "effective amount" refers to an amount effective to achieve the desired therapeutic or prophylactic effect at the desired dose and time. The "therapeutically effective amount" of a substance may vary depending on factors such as disease state, age, gender and body weight of an individual and the ability of the substance/molecule to elicit a desired response in the individual. In the case of cancer, the therapeutically effective amount of an ADC can reduce the number of cancer cells; reduce the tumor volume; inhibit the cancer cells infiltrating into the surrounding organs; inhibit tumor metastasis; inhibit the growth of tumor; and/or alleviate to some extent one or more symptoms associated with cancer. For the prophylaxis or treatment of the disease, the appropriate dosage of the ADC of the present disclosure will depend on the type of disease to be treated, the type of the antibody-drug conjugate, the severity and progression of the disease, the administration of the ADC, etc. Suitably, the antibody-drug conjugate is administered to the patient either once or through a series of treatments. Depending on the type and severity of the disease, the dose administered to the patient may be about 1 μg/kg to 100 mg/kg (0.1 mg/kg to 20 mg/kg) of the ADC, for example or by one or more separate admistrations or by continuous infusion. Depending on the factors described above, the typical daily dose may range from about 1 μg/kg to 100 mg/kg or more. For repeated administrations for several days or more, depending on the conditions, the treatment is usually continued until the desired inhibition of symptoms appears. An exemplary dose of the antibody-drug conjugate may range from about 0.05 mg/kg to about 10 mg/kg. As such, the antibody-drug conjugate of one or more doses of about 0.5 mg/kg, 2.0 mg/kg, 4.0 mg/kg or 10 mg/kg (or any combination thereof) may be administered to the patient. Such doses may be administered intermittently, for example, weekly or every three weeks (e.g., such that the patient receives about 2 to about 20 doses, or, for example, about 6 doses of the antibody-drug conjugate). A higher initial loading dose may be administered, followed by one or more doses of lower dose. The process of this therapy is easily monitored by conventional techniques and assays.

"Pharmaceutically acceptable carriers" include, when used in the present disclosure, pharmaceutically acceptable carriers, excipients or stabilizers, which are non-toxic to the cells or mammals to which they are exposed at the dosage and concentration employed. Typically, a physiologically acceptable carrier is a pH buffered aqueous solution. Examples of physiologically acceptable carriers include buffers such as phosphates, citrates and other organic acids; antioxidants including ascorbic acid; low molecular weight (less than about 10 residues) polypeptides; proteins such as serum albumin, gelatin or immunoglobulins; hydrophilic polymers such as polyvinylpyrrolidone; amino acids such as glycine, glutamine, asparagine, arginine or lysine; monosaccharides, disaccharides and other carbohydrates, including glucose, mannose, sucrose, trehalose or dextrin; chelating agents such as EDTA; sugar alcohols such as mannitol or sorbitol; salt-forming counterions such as sodium; and/or nonionic surfactants.

In the present disclosure, the drug load or drug to antibody ratio, i.e., the average number of cytotoxic drug modules of each antibody in the ADC can range from 1 to 12 drug per antibody, for example, about 1, about 2, about 1 about 4, about 5, about 6, about 7, about 8, about 9, about 10, about 11, or about 12. Different attachment sites can be used, e.g., through interchain disulfide bonds between heavy and light chains, through interchain disulfide bonds between heavy chains in hinge region, on engineered cysteine, on selected Lys residues on each chain, on carbohydrate, on terminal residues. The average number of drug modules per antibody from the ADC preparation of coupling reaction can be verified by conventional means, such as mass spectrometry, ELISA assay, and HPLC, in certain embodiments, the ADCs of the present disclosure can have a drug load ranging from 1 to about 8: from about 4 to about 12, from about 2 to about 6; from about 3 to about 5; from about 4 to about 5; from about 3.5 to about 4.5; about 4. In certain embodiments, to produce reactive thiol group for the linking of the linker to the antibody, the antibody may be reduced under partial or complete reductive conditions to produce a reactive cysteine thiol group.

In the present disclosure, the pharmaceutically acceptable salts of the ADCs include acid addition salts of inorganic acids, carboxylic acids and sulfonic acids, for example, salts of the following acids: hydrochloric acid, hydrobromic acid, sulfuric acid, phosphoric acid, methanesulfonic acid, ethanesulfonic acid, benzenesulfonic acid, toluenesulfonic acid, naphthalene disulfonic acid, acetic acid, trifluoroacetic acid, propionic acid, lactic acid, tartaric acid, malic acid, citric acid, fumaric acid, maleic acid and benzoic acid.

The pharmaceutically acceptable salts of the antibody-drug conjugates of the present disclosure also include salts of conventional bases, for example alkali metal salts (e.g., sodium salts and potassium salts), alkaline earth metal salts (e.g., calcium salts and magnesium salts) and ammonium salts derived from ammonia or organic amines containing from 1 to 16 carbon atoms, in which the organic amines are, for example, ethylamine, diethylamine, triethylamine, ethyl diisopropylamine, monoethanolamine, diethanolamine, triethanolamine, dicyclohexylamine, dimethylaminoethanol, procaine, dibenzamide, N-methylpiperidine, N-methylmorpholine, arginine, lysine and 1,2-ethylenediamine.

The target protein-associated tumors that can be treated with the ADCs of the invention include tumors with target overexpression. For example, EGFR associated tumors include respiratory tract tumors (e.g., small cell carcinoma and non-small cell carcinoma, bronchial carcinoma); tumors of digestive tracts (e.g., esophagus, stomach, gallbladder, small intestine, large intestine, rectum); tumors of endocrine and exocrine glands (e.g thyroid and parathyroid, pancreas and salivary glands); tumors of head and neck regions (e.g., larynx, hypopharynx, nasopharynx, oropharynx, lips, mouth, tongue and esophagus); and/or gliomas. HER2-associated tumors include bladder cancers, esophageal cancers, breast cancers, cervical cancers, gastric adenocarcinomas, etc.

The ADCs of the present disclosure may be used in combination with a known chemotherapeutic agent for the treatment of tumors. The chemotherapeutic agent can be, for example, Adriamycin, cyclophosphamide and taxane [Taxol and Taxotere], Xeloda, Gemzar, Navelbine, Tamoxifen, aromatase inhibitors (Arimidex, Femara, Aromasin), 5-FU plus folinic acid, camptosar, oxaliplatin, cisplatin, carboplatin, estramustine, Novantrone, prednisone, Oncovin, etc., or a combination thereof.

EXAMPLES

A summary list of the tetravalent antibodies prepared is shown in Table 1 below.

TABLE 1

| ID | Protein Structure (Long/Short Chain) | SEQ ID No. (long chain) | SEQ ID No. (short chain) |
|---|---|---|---|
| BB01H | VHCH1Fc(g1)(G$_3$S)$_4$VHCH1/VLCL(κ) | 1 | 2 |
| BB01E | VHCH1Fc(g2)(G$_3$S)$_4$VHCH1/VLCL(λ) | 3 | 4 |
| BB02E | VHCH1Fc(g1)(G$_3$S)$_4$VHCH1/VLCL(κ) | 5 | 6 |
| BB03E | VHCH1Fc(g1)(G$_3$S)$_4$VHCH1/VLCL(κ) | 7 | 8 |
| BB04E | VHCH1Fc(g2)(G$_3$S)$_1$VHCH1/VLCL(κ) | 9 | 10 |
| BB05E | VLCL(κ)Fc(g1)(G$_3$S)$_4$VLCL(κ)/VHCH1 | 11 | 12 |
| BB02H | VHCH1Fc(g1)(G$_3$S)$_4$VHCH1/VLCL(κ) | 13 | 14 |
| BB03H | VLCL(κ)Fc(g1)(G$_3$S)$_4$VLCL(κ)/VHCH1 | 15 | 16 |
| BB04H | VLCL(κ)Fc(g1)(G$_3$S)$_4$VLCL(κ)/VHCH1 | 17 | 18 |
| BB06E | VLCL(κ)Fc(g1)(G$_3$S)$_4$VLCL(κ)/VHCH1 | 19 | 20 |
| BB01M | VHCH1Fc(g1)(G$_3$S)$_4$VHCH1/VLCL(κ) | 21 | 22 |
| BB02M | VLCL(κ)Fc(g1)(G$_3$S)$_4$VLCL(κ)/VHCH1 | 23 | 24 |

1. Preparation of Tetravalent Antibodies

Example tetravalent antibodies were designed and synthesized using sequences in Table 1 fused with constant isotype of choice. In some examples, certain point mutations are introduced for specific purpose. Two types of tetravalent antibodies were prepared, conventional and twisted formats. Each tetravalent antibody contains two long chains and four short chains. For conventional format, the sequences of the long chain contain a full-length heavy chain and an intact VH-CH1 fragment of the same antibody fused to the C-terminus of Fc through a flex (GS) linker. The short chain sequences are the same as the light chain of the same antibody.

For twisted format, the sequences of the long chains contain a full length light chain (VL-CL) directly fused to the N-terminus of Fc (CH2-CH3) and another full length light chain (VL-CL) (of the same antibody) fused to the C-terminus of Fc through a flex (GS) linker. The sequences of the short chains contain the full length of VH-CH1 of the same antibody.

For expression of the engineered tetravalent antibodies, codon optimization and gene synthesis were performed. Specific full-length long chain and short chain DNA were each cloned into a separate pcDNA3 plasmid. HEK293 cell transient transfection of the paired plasmids and one-step Protein A purification was used to prepare sufficient amount of proteins for testing.

Example tetravalent antibodies:
(a) BB01H: BB01H is made in conventional format of IgG$_1$κ isotype, where its long chain contains: VH-CH1-CH2-CH3-(G$_2$S)$_4$—VH-CH1, and short chain contains: CL-CL(κ). As used in the sequence of a tetravalent antibody described herein, VH, VL, CH1, CH2, CH3 refer to the domains or fragments of the precursor antibody from which the tetravalent antibody is constructed. Sequence of the long chain of BB01H is shown as SEQ ID NO:1. Sequence of the short chain of BB01H is shown as SEQ ID NO:2.

(b) BB01E: BB01E is prepared in conventional format of IgG$_2$λ isotype, where its long chain contains VH-CH1-CH2-CH3-(G$_3$S)$_4$—VH-CH1 (CH2-CH3 of IgG2 is also referred to as Fc(g2)), and short chain contains VL-CL(λ). Sequence of the long chain of BB01E is shown as SEQ ID NO:3. Sequence of short chain of BB01E is shown as SEQ ID NO:4.

(c) BB04E: BB04E is made in conventional format of IgG$_2$K isotype, where its long chain contains: VH-CH1-CH2-CH3-(G$_3$S)$_1$—VH-CH1, and short chain contains: VL-CL(κ). Sequence of the long chain of BB04E is shown as SEQ ID NO:9. Sequence of the short chain of BB04E is shown as SEQ ID NO:10.

(d) BB05E: BB05E is made in twisted format of IgG$_1$κ isotype, where its long chain contains: VL-CL(κ)-CH2-CH3(G$_3$S)$_4$—VL-CL(κ), and short chain contains: VH-CH1(IgG1). Sequence of the long chain of BB05E is shown as SEQ ID NO:11. Sequence of the short chain of BB05E is shown as SEQ ID NO:12.

2. Preparation of Tetravalent ADCs

Tetravalent antibodies (BB01E, BB02E, BB03E, BB04E, BB05E) and control bivalent antibody (Ctl) are conjugated to the cytotoxic agents (e.g., MMAE, DM1) via a linker. Antibody in phosphate buffer at neutral pH is added TCEP for partial reduction. Drug-linker (MC-val-cit-PAB-MMAE or MC-DM1) in DMA is added and allowed to react with tetrabody to obtain desired drug-to-antibody ratio (DAR).

Tetravalent antibody in phosphate buffer is added OSu-Glu-val-cit-PAB-MMAE in DMA, and allowed to react to obtain desired DAR.

3. Characterization of Tetravalent Antibodies and Tetravalent ADCs (a) Hydrophobic Interaction Chromatography (HIC): HIC is used for the evaluation of drug distribution and molar ratio of drug and antibody in ADC.

Figure 2:
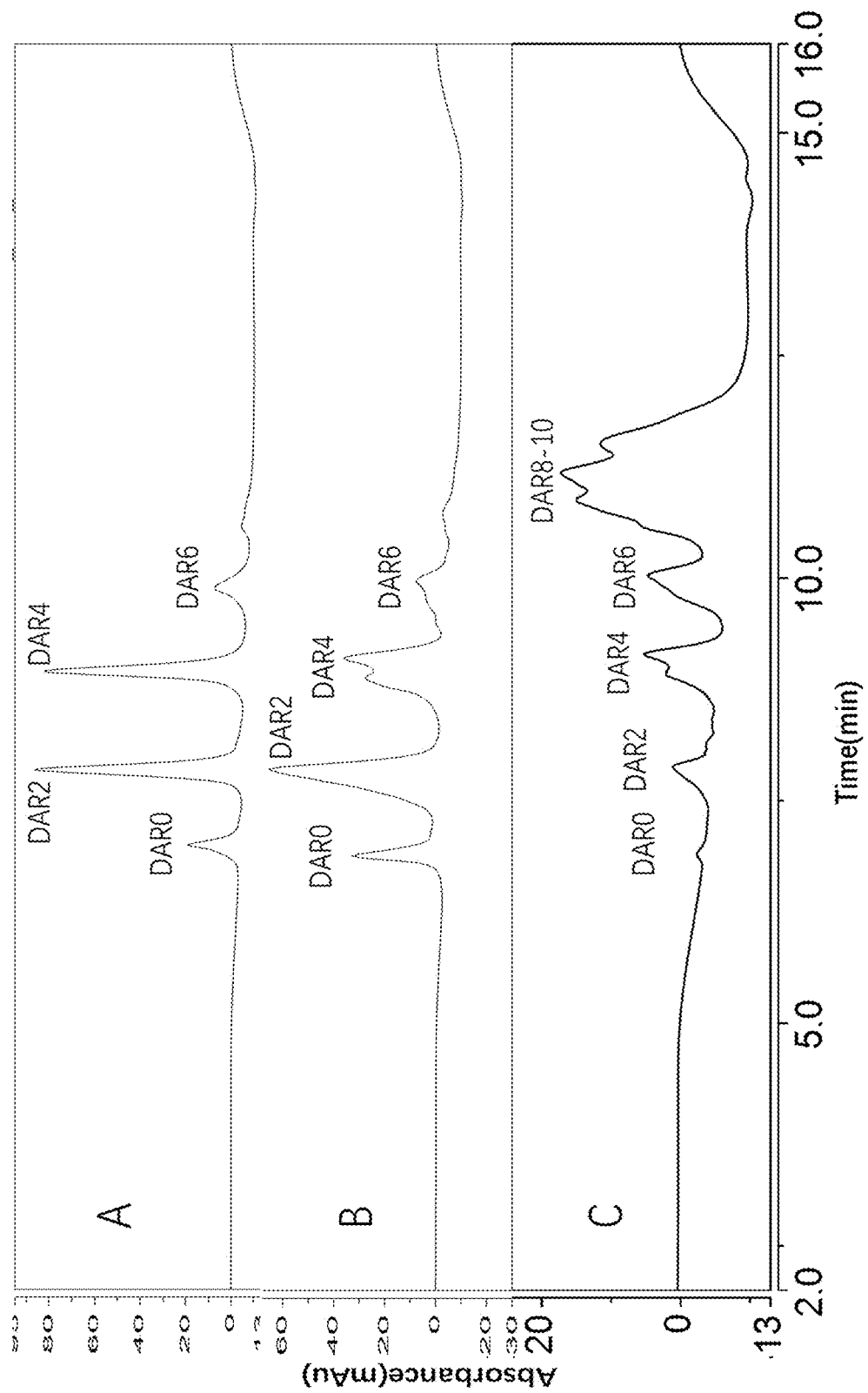
FIG. 2 is a comparison diagram of HIC profiles of certain tetravalent ADCs of some embodiments of the present disclosure and control ADC. Panel A: Ctl-MMAE; Panel B: BB01E-MMAE with low DAR; Panel C: BB01E-MMAE with high DAR.

Ctl-MMAE (bivalent ADC), BB01E-MMAE (tetravalent ADC) with low DAR, and BB01E-MMAE with high DAR were analyzed by HIC, and the representative HIC chromatograms are presented in FIG. 2. For Ctl-MMAE (bivalent ADC) and BB01E-MMAE with low DAR, the main peaks are antibodies linked to 2 and 4 drug molecules (DAR2, DAR4, respectively), and the minor peaks are antibodies (DAR0) and antibodies linked to 6 and 8 drug molecules (DAR6, DAR8). The results indicate BB01E-MMAE and Ctl-MMAE have similar drug distribution and DAR values. BB01E-MMAE with high DAR mainly contains antibodies linked to 8 and 10 drug molecules (DAR8, DAR10).

(b) Binding (b1) Binding to recombinant expressed target proteins.

ELISA assay is used to exam and compare the target binding capabilities (to EGFR or HER2) between the tetravalent antibodies and control bivalent antibodies. Tetravalent antibody samples or control antibodies diluted in 5-fold serial dilutions starting from 20 μg/mL and 8 dilutions total, were coated onto 96-well plates and the plates were incubated at 4° C. overnight. Using HRP-labeled human target protein (EGFR or HER2 at 5 ng/mL) as a detection agent and TMB for colorimetric reaction, the plates read at 450/650 nm for absorbance on Microplate Reader (Molecular Devices, SpectraMax 190) and data analysis was performed using a dose response curve format four parameters logistic model.

Figure 3:
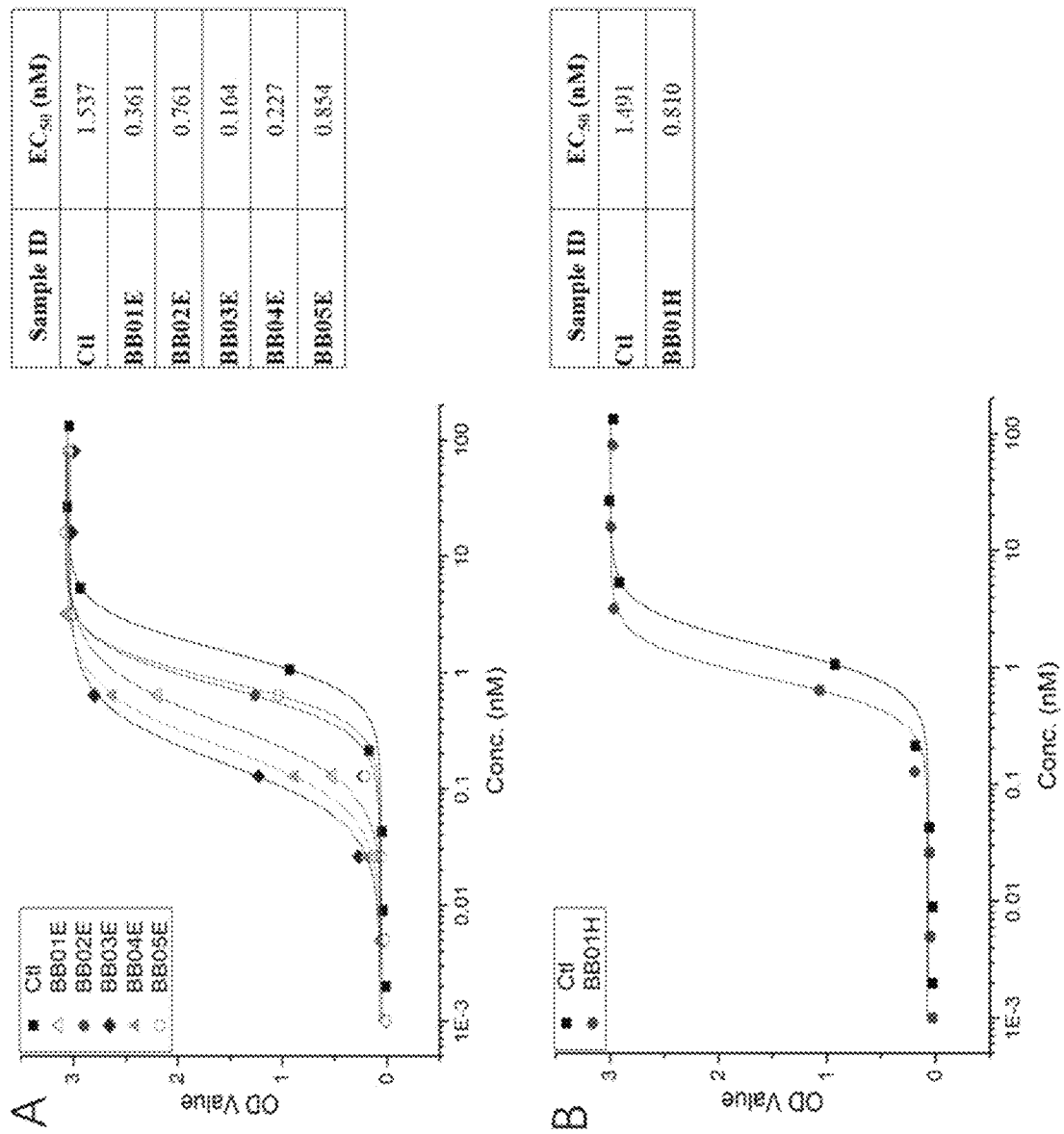
FIG. 3 shows ELISA binding results of tetravalent antibodies of some embodiments of the present disclosure and control antibody. Panel A: EGFR-binding results; Panel B: HER2-binding results.

The results in FIG. 3 showed that all tetravalent antibody variants bound to their specific target proteins with enhanced capabilities in comparison with the control bivalent antibodies.

(b2) Binding to EGFR-expressing cancer cells

FACS assay on several cancer cell lines (MDA-MB-468, NUGC3) with different levels of surface EGFR was used to analyze binding activity of tetravalent antibodies to EGFR-expressing cell lines and compared with that of the bivalent control. Briefly, single cell suspension was first stained with tetravalent antibody samples or control antibody at saturate concentration (10 μg/mL) and then stained with FITC-labeled anti-human kappa antibody as a secondary antibody.

Figure 4:
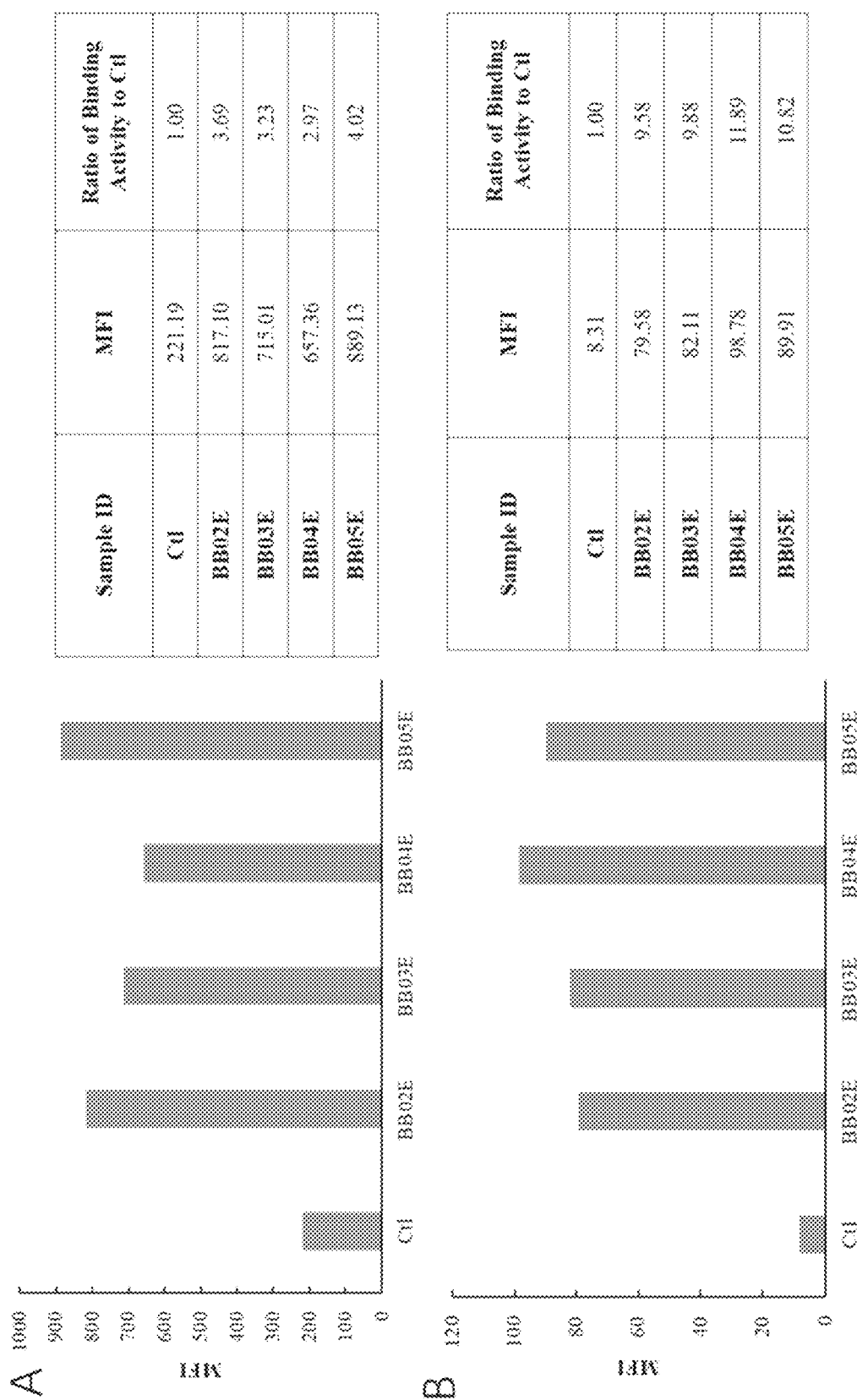
FIG. 4 shows FACS analysis of tetravalent anti-EGFR antibodies of some embodiments of the present disclosure and control antibody. Panel A: EGFR high-expressing MDA-MB-468 cells; Panel B: EGFR low-expressing NUGC3 cells.

The results in FIG. 4 showed that the mean fluorescent intensity (MFI) of tetravalent anti-EGFR antibodies bound onto EGFR high-expressing MDA-MB468 cells were 3-4-fold higher than that of bivalent control. The MFI differences were even greater on EGFR low-expressing NUGC3 cells (nearly 10-fold differences). Although the two more copies of kappa on tetravalent antibody might contribute to a higher signal (two-fold), the significantly higher MFI (3-10 fold) of tetravalent antibody staining suggest that the four targeting arms on tetravalent format offered significantly more efficient synergy when binding to targets than the two arms on bivalent format. This synergistic effect was more pronounce when binding to EGFR low-expressing cells than to EGFR high-expressing cells.

(c) Internalization

Figure 5:
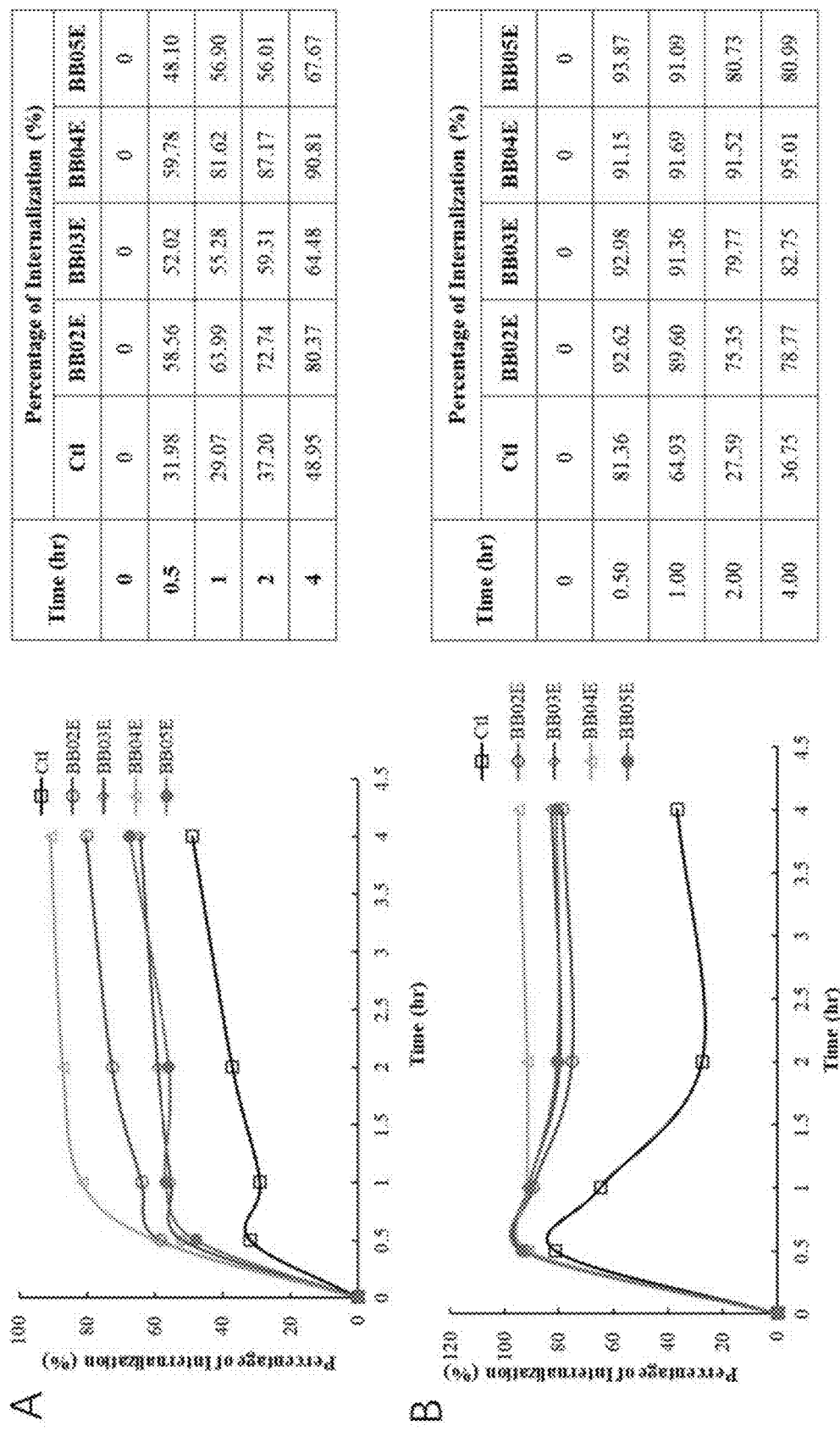
FIG. 5 shows internalization analysis of tetravalent anti-EGFR antibodies of some embodiments of the present disclosure and control antibody. Panel A: EGFR high-expressing MDA-MB-468 cells; Panel B: EGFR low-expressing NUGC3 cells.

Tetravalent antibody induced internalization of antibody-target complex was analyzed on several cancer cell lines (MDA-MB-468, NUGC3) with different levels of surface EGFR and compare with that of the bivalent control. To do the assay, single cell suspensions were first incubated with antibody samples (10 μg/mL) on ice for 1 hr and then washed to remove unbound antibodies. While one aliquot remained on ice, the rest were incubated at 37□ for different period of time (0.5, 1, 2 and 4 hrs). At the end of each defined incubation time, an aliquot of cells was taken out of the 37□ incubator and put on ice. When the longest incubation finished, all aliquots were stained with FITC-labeled secondary antibody and stained samples were analyzed by flow cytometry. Receptor-antibody complex internalization was calculated as percent MFI loss at 37□ in relative to that on ice after subtracting the background value of MFI derived from the stained control. Percentage internalization was calculated according to: percent of internalization (%)= $(MFI_{0h} - MFI_{other\ times})/MFI_{0h}$ The results in FIG. 5 showed that, on both EGFR high-expressing MDA-MB-468 cells and EGFR low-expressing NUGC3 cells, the percent of internalized tetravalent antibodies was higher than that of the bivalent control, suggesting that the internalization potential of tetravalent antibodies in EGFR-positive human cancer cells was significantly enhanced over that of the bivalent control.

Similar internalization analysis was performed for tetravalent ADC and conventional ADC as controls. In all cases, tetravalent ADC with either MMAE payload or DM1 payload, internalized more efficiently than conventional bivalent ADC (FIGS. 6A-6C).

(d) Cytotoxicity

To investigate whether the enhanced internalization of tetravalent antibodies and ADCs would translate into more potent cytotoxicity, in vitro cytotoxicity to target expressing cancer cells with varying EGFR expression levels was evaluated in comparison with conventional bivalent-ADC in a colorimetric-based cytotoxic assay. To perform the assay, target cells were seeded into a 96-well flat-bottom tissue culture plate at an optimized cell density for each cell line and incubated at 37° C., 5% CO₂ overnight (16-20 hrs). Serial dilutions of ADC samples were transferred to cell plate and the assay plates were incubated for a defined period of time (3-5 days depend on cell lines) for optimal killing.

The results in FIGS. 7A-7C showed that various tetravalent ADC product with either MMAE payload or DM1 payload, had more potent cytotoxicity than conventional bivalent ADC to target expressing cells.

While specific embodiments of the present invention have been described in detail, those skilled in the art will understand that various modifications and substitutions can be made to those details according to all teachings that have been disclosed, and all of these changes fall within the scope of the present invention. The full scope of the invention is given by the appended claims and any equivalents thereof.

```
                        Sequence Listing

BB01H
Chain 1 (long chain, SEQ ID NO: 1):
EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGT
LVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCDKTHTCPPCPA
PEAAGGPSVFLFPPKPKDTLMISRTPEVTCVVVDVSHEDPEVKENWYVDGVEVHNAKT
KPREEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGKGGGSGGGSGGGSGGGS
EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGT
LVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSC Chain 2 (short chain, SEQ ID NO: 2):
DIQMTQSPSSLSASVGDRVTITCRASQDVNTAVAWYQQKPGKAPKLLIYSASFLYSGVP
SRFSGSRSGTDFTLTISSLQPEDFATYYCQQHYTTPPTFGQGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC BB01E
Chain 1 (long chain, SEQ ID NO: 3):
QVQLKQSGPGLVQPSQSLSITCTVSGFSLTNYGVHWVRQSPGKGLEWLGVIWSGGNTD
YNTPFTSRLSINKDNSKSQVFFKMNSLQSNDTAIYYCARALTYYDYEFAYWGQGTLVT
VSAASTKGPSVFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSR
EEMTKNQVSLTCLVKGFYPSDISVEWESNGQPENNYKTTPPMLDSDGSFFLYSKLTVDK
SRWQQGNVFSCSVMHEALHNHYTQKSLSLSPGKGGGSGGGSGGGSGGGSQVQLKQSG
PGLVQPSQSLSITCTVSGFSLTNYGVHWVRQSPGKGLEWLGVIWSGGNTDYNTPFTSRL
SINKDNSKSQVFFKMNSLQSNDTAIYYCARALTYYDYEFAYWGQGTLVTVSAASTKGP
SVFPLAPCSRSTSESTAALGCLVKDYFPEPVTVSWNSGALTSGVHTFPAVLQSSGLYSLS
SVVTVPSSNFGTQTYTCNVDHKPSNTKVDKTV Chain 2 (short chain, SEQ ID NO: 4): VL-CL(λ):
DILLTQSPVILSVSPGERVSFSCRASQSIGTNIHWYQQRTNGSPRLLIKYASESISGIPSRES
GSGSGTDFTLSINSVESEDIADYYCQQNNNWPTTFGAGTKLELKGQPKANPTVTLFPPSS
EELQANKATLVCLISDFYPGAVTVAWKADGSPVKAGVETTKPSKQSNNKYAASSYLSL
TPEQWKSHRSYSCQVTHEGSTVEKTVAPTECS BB02E
Chain 1 (long chain, SEQ ID NO: 5):
QVQLKQSGPGLVQPSQSLSITCTVSGFSLTNYGVHWVRQSPGKGLEWLGVIWSGGNTD
YNTPFTSRLSINKDNSKSQVFFKMNSLQSDDTAIYYCARALTYYDYEFAYWGQGTLVT
VSAASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPE
AAGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGKGGGSGGGSGGGSGGGSQVQ
LKQSGPGLVQPSQSLSITCTVSGFSLTNYGVHWVRQSPGKGLEWLGVIWSGGNTDYNTP
FTSRLSINKDNSKSQVFFKMNSLQSDDTAIYYCARALTYYDYEFAYWGQGTLVTVSAAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSC Chain 2 (short chain, SEQ ID NO: 6):
DILLTQSPVILSVSPGERVSFSCRASQSIGTNIHWYQQRTNGSPRLLIKYASESISGIPSRES
GSGSGTDFTLSINSVESEDIADYYCQQNNNWPTTFGAGTKLELKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC
```

Sequence Listing

BB03E
Chain 1 (long chain, SEQ ID NO: 7):
QVQLQESGPGLVKPSETLSLTCTVSGGSVSSGDYYWTWIRQSPGKGLEWIGHIYYSGNT
NYNPSLKSRLTISIDTSKTQFSLKLSSVTAADTAIYYCVRDRVTGAFDIWGQGTMVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEAAGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPGKGGGSGGGSGGGSGGGSQVQLQESG
PGLVKPSETLSLTCTVSGGSVSSGDYYWTWIRQSPGKGLEWIGHIYYSGNTNYNPSLKS
RLTISIDTSKTQFSLKLSSVTAADTAIYYCVRDRVTGAFDIWGQGTMVTVSSASTKGPSV
FPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSC Chain 2 (short chain, SEQ ID NO: 8):
DIQMTQSPSSLSASVGDRVTITCQASQDISNYLNWYQQKPGKAPKLLIYDASNLETGVPS
RFSGSGSGTDFTFTISSLQPEDIATYFCQHFDHLPLAFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC BB04E
Chain 1 (long chain, SEQ ID NO: 9):
QVQLKQSGPGLVQPSQSLSITCTVSGFSLTNYGVHWVRQSPGKGLEWLGVIWSGGNTD
YNTPFTSRLSINKDNSKSQVFFKMNSLQSDDTAIYYCARALTYYDYEFAYWGQGTLVT
VSAASTKGPSVFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSR
EEMTKNQVSLTCLVKGFYPSDISVEWESNGQPENNYKTTPPMLDSDGSFFLYSKLTVDK
SRWQQGNVFSCSVMHEALHNHYTQKSLSLSPGKGGGSQVQLKQSGPGLVQPSQSLSITC
TVSGFSLTNYGVHWVRQSPGKGLEWLGVIWSGGNTDYNTPFTSRLSINKDNSKSQVFFK
MNSLQSDDTAIYYCARALTYYDYEFAYWGQGTLVTVSAASTKGPSVFPLAPCSRSTSES
TAALGCLVKDYFPEPVTVSWNSGALTSGVHTFPAVLQSSGLYSLSSVVTVPSSNFGTQT
YTCNVDHKPSNTKVDKTV Chain 2 (short chain, SEQ ID NO: 10):
DILLTQSPVILSVSPGERVSFSCRASQSIGTNIHWYQQRTNGSPRLLIKYASESISGIPSRES
GSGSGTDFTLSINSVESEDIADYYCQQNNNWPTTFGAGTKLELKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC BB05E
Chain 1 (long chain, SEQ ID NO: 11):
DILLTQSPVILSVSPGERVSFSCRASQSIGTNIHWYQQRTNGSPRLLIKYASESISGIPSRFS
GSGSGTDFTLSINSVESEDIADYYCQQNNNWPTTFGAGTKLELKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGECDKTHTCPPCPAPEAAGGPSVFLFPPKP
KDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNV
FSCSVMHEALHNHYTQKSLSLSPGKGGGSGGGSGGGSGGGSDILLTQSPVILSVSPGERV
SFSCRASQSIGTNIHWYQQRTNGSPRLLIKYASESISGIPSRFSGSGSGTDFTLSINSVESED
IADYYCQQNNNWPTTFGAGTKLELKRTVAAPSVFIFPPSDEQLKSGTASVVCLLNNFYP
REAKVQWKVDNALQSGNSQESVTEQDSKDSTYSLSSTLTLSKADYEKHKVYACEVTHQ
GLSSPVTKSFNRGEC Chain 2 (short chain, SEQ ID NO: 12):
QVQLKQSGPGLVQPSQSLSITCTVSGFSLTNYGVHWVRQSPGKGLEWLGVIWSGGNTD
YNTPFTSRLSINKDNSKSQVFFKMNSLQSDDTAIYYCARALTYYDYEFAYWGQGTLVT
VSAASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSC BB02H
Chain 1 (long chain, SEQ ID NO: 13):
EVQLVESGGGLVQPGGSLRLSCAASGFTFTDYTMDWVRQAPGKGLEWVADVNPNSGG
SIYNQRFKGRFTLSVDRSKNTLYLQMNSLRAEDTAVYYCARNLGPSFYFDYWGQGTLV
TVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPE
AAGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGKGGGSGGGSGGGSGGGSEVQ
LVESGGGLVQPGGSLRLSCAASGFNIKDTYIHWVRQAPGKGLEWVARIYPTNGYTRYA
DSVKGRFTISADTSKNTAYLQMNSLRAEDTAVYYCSRWGGDGFYAMDYWGQGTLVT VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSC Chain 2 (short chain, SEQ ID NO: 14):
DIQMTQSPSSLSASVGDRVTITCKASQDVSIGVAWYQQKPGKAPKLLIYSASYRYTGVPS
RFSGSGSGTDFTLTISSLQPEDFATYYCQQYYIYPYTFGQGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC BB03H
Chain 1 (long chain, SEQ ID NO: 15):
DIQMTQSPSSLSASVGDRVTITCKASQDVSIGVAWYQQKPGKAPKLLIYSASYRYTGVPS
RFSGSGSGTDFTLTISSLQPEDFATYYCQQYYIYPYTFGQGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPEAAGGPSVFLFPPK
PKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNV
FSCSVMHEALHNHYTQKSLSLSPGKGGGSGGGSGGGSGGGSDIQMTQSPSSLSASVGDR
VTITCKASQDVSIGVAWYQQKPGKAPKLLIYSASYRYTGVPSRFSGSGSGTDFTLTISSLQ
PEDFATYYCQQYYIYPYTFGQGTKVEIKRTVAAPSVFIFPPSDEQLKSGTASVVCLLNNF
YPREAKVQWKVDNALQSGNSQESVTEQDSKDSTYSLSSTLTLSKADYEKHKVYACEVT
HQGLSSPVTKSFNRGEC Chain 2 (short chain, SEQ ID NO: 16)
EVQLVESGGGLVQPGGSLRLSCAASGFTFTDYTMDWVRQAPGKGLEWVADVNPNSGG
SIYNQRFKGRFTLSVDRSKNTLYLQMNSLRAEDTAVYYCARNLGPSFYFDYWGQGTLV
TVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSC BB04H
Chain 1 (long chain, SEQ ID NO: 17):
DIQMTQSPSSLSASVGDRVTITCRASQDVNTAVAWYQQKPGKAPKLLIYSASFLYSGVP
SRFSGSRSGTDFTLTISSLQPEDFATYYCQQHYTTPPTFGQGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGECDKTHTCPPCPAPEAAGGPSVFLFP
PKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQG
NVFSCSVMHEALHNHYTQKSLSLSPGKGGGSGGGSGGGSGGGSDIQMTQSPSSLSASVG
DRVTITCRASQDVNTAVAWYQQKPGKAPKLLIYSASFLYSGVPSRFSGSRSGTDFTLTIS
SLQPEDFATYYCQQHYTTPPTFGQGTKVEIKRTVAAPSVFIFPPSDEQLKSGTASVVCLL
NNFYPREAKVQWKVDNALQSGNSQESVTEQDSKDSTYSLSSTLTLSKADYEKHKVYAC
EVTHQGLSSPVTKSFNRGEC Chain 2 (short chain, SEQ ID NO: 18):
EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGT
LVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSC BB06E
Chain 1 (long chain, SEQ ID NO: 19):
DIQMTQSPSSLSASVGDRVTITCQASQDISNYLNWYQQKPGKAPKLLIYDASNLETGVPS
RFSGSGSGTDFTFTISSLQPEDIATYFCQHFDHLPLAFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGECDKTHTCPPCPAPEAAGGPSVFLFPPK
PKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNV
FSCSVMHEALHNHYTQKSLSLSPGKGGGSGGGSGGGSGGGSDIQMTQSPSSLSASVGDR
VTITCQASQDISNYLNWYQQKPGKAPKLLIYDASNLETGVPSRFSGSGSGTDFTFTISSLQ
PEDIATYFCQHFDHLPLAFGGGTKVEIKRTVAAPSVFIFPPSDEQLKSGTASVVCLLNNFY
PREAKVQWKVDNALQSGNSQESVTEQDSKDSTYSLSSTLTLSKADYEKHKVYACEVTH
QGLSSPVTKSFNRGEC Chain 2 (short chain, SEQ ID NO: 20):
QVQLQESGPGLVKPSETLSLTCTVSGGSVSSGDYYWTWIRQSPGKGLEWIGHIYYSGNT
NYNPSLKSRLTISIDTSKTQFSLKLSSVTAADTAIYYCVRDRVTGAFDIWGQGTMVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSC BB01M
Chain 1 (long chain, SEQ ID NO: 21):
EVQLVESGGGLVQPGGSLRLSCAASGYTFTSYWLHWVRQAPGKGLEWVGMIDPSNSD
TRFNPNFKDRFTISADTSKNTAYLQMNSLRAEDTAVYYCATYRSYVTPLDYWGQGTLV
TVSSASTKGPSVFPLAPSSKSTSGGTAALGCLVKDYFPEPVTVSWNSGALTSGVHTFPAV

Sequence Listing

```
LQSSGLYSLSSVVTVPSSSLGTQTYICNVNHKPSNTKVDKRVEPKSCDKTHTCPPCPAPE
AAGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGKGGGSGGGSGGGSGGGSEVQ
LVESGGGLVQPGGSLRLSCAASGYTFTSYWLHWVRQAPGKGLEWVGMIDPSNSDTREN
PNFKDRFTISADTSKNTAYLQMNSLRAEDTAVYYCATYRSYVTPLDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSC

Chain 2 (short chain, SEQ ID NO: 22):
DIQMTQSPSSLSASVGDRVTITCKSSQSLLYTSSQKNYLAWYQQKPGKAPKLLIYWAST
RESGVPSRFSGSGSGTDFTLTISSLQPEDFATYYCQQYYAYPWTFGQGTKVEIKRTVAAP
SVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC BB02M
Chain 1 (long chain, SEQ ID NO: 23):
DIQMTQSPSSLSASVGDRVTITCKSSQSLLYTSSQKNYLAWYQQKPGKAPKLLIYWAST
RESGVPSRFSGSGSGTDFTLTISSLQPEDFATYYCQQYYAYPWTFGQGTKVEIKRTVAAP
SVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGECDKTHTCPPCPAPEAAGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPGKGGGSGGGSGGGSGGGSDIQMTQSPS
SLSASVGDRVTITCKSSQSLLYTSSQKNYLAWYQQKPGKAPKLLIYWASTRESGVPSRFS
GSGSGTDFTLTISSLQPEDFATYYCQQYYAYPWTFGQGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC Chain 2 (short chain, SEQ ID NO: 24):
EVQLVESGGGLVQPGGSLRLSCAASGYTFTSYWLHWVRQAPGKGLEWVGMIDPSNSD
TRFNPNFKDRFTISADTSKNTAYLQMNSLRAEDTAVYYCATYRSYVTPLDYWGQGTLV
TVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSC Antibody Antigen-Binding Site Partial Sequence
Chain 1 (SEQ ID NO: 25) (underlined portions indicate CDR1, CDR2, CDR3):
EVQLVESGGGLVQPGGSLRLSCAASGFNIKDTYIHWVRQAPGKGLEWVARIYPTNGYTRYADSV
KGRFTISADTSKNTAYLQMNSLRAEDTAVYYCSRWGGDGFYAMDYWGQGTLVTVSS Chain 2 (SEQ ID NO: 26) (underlined portions indicate CDR1, CDR2, CDR3):
DIQMTQSPSSLSASVGDRVTITCRASQDVNTAVAWYQQKPGKAPKLLIYSASFLYSGVPSRFSGS
RSGTDFTLTISSLQPEDFATYYCQQHYTTPPTFGQGTKVEIK Antibody Antigen-Binding Site Partial Sequence
Chain 1 (SEQ ID NO: 27) (underlined portions indicate CDR1, CDR2, CDR3):
EVQLVESGGGLVQPGGSLRLSCAASGFTFTDYTMDWVRQAPGKGLEWVADVNPNSGGSIYNQR
FKGRFTLSVDRSKNTLYLQMNSLRAEDTAVYYCARNLGPSFYFDYWGQGTLVTVSS Chain 2 (SEQ ID NO: 28) (underlined portions indicate CDR1, CDR2, CDR3):
DIQMTQSPSSLSASVGDRVTITCKASQDVSIGVAWYQQKPGKAPKLLIYSASYRYTGVPSRFSGS
GSGTDFTLTISSLQPEDFATYYCQQYYIYPYTFGQGTKVEIK Antibody Antigen-Binding Site Partial Sequence
Chain 1 (SEQ ID NO: 29) (underlined portions indicate CDR1, CDR2, CDR3):
QVQLKQSGPGLVQPSQSLSITCTVSGFSLTNYGVHWVRQSPGKGLEWLGVIWSGGNTDYNTPFT
SRLSINKDNSKSQVFFKMNSLQSDDTAIYYCARALTYYDYEFAYWGQGTLVTVSA Chain 2 (SEQ ID NO: 30) (underlined portions indicate CDR1, CDR2, CDR3):
DILLTQSPVILSVSPGERVSFSCRASQSIGTNIHWYQQRTNGSPRLLIKYASESISGIPSRFSGSGSGT
DFTLSINSVESEDIADYYCQQNNNWPTTFGAGTKLELK Antibody Antigen-Binding Site Partial Sequence
Chain 1 (SEQ ID NO: 31) (underlined portions indicate CDR1, CDR2, CDR3):
QVQLQESGPGLVKPSETLSLTCTVSGGSVSSGDYYWTWIRQSPGKGLEWIGHIYYSGNTNYNPSL
KSRLTISIDTSKTQFSLKLSSVTAADTAIYYCVRDRVTGAFDIWGQGTMVTVSS Chain 2 (SEQ ID NO: 32) (underlined portions indicate CDR1, CDR2, CDR3):
DIQMTQSPSSLSASVGDRVTITCQASQDISNYLNWYQQKPGKAPKLLIYDASNLETGVPSRFSGS
GSGTDFTFTISSLQPEDIATYFCQHFDHLPLAFGGGTKVEIK Antibody Antigen-Binding Site Partial Sequence
Chain 1 (SEQ ID NO: 33) (underlined portions indicate CDR1, CDR2, CDR3):
EVQLVESGGGLVQPGGSLRLSCAASGYTFTSYWLHWVRQAPGKGLEWVGMIDPSNSDTRFNPN
FKDRFTISADTSKNTAYLQMNSLRAEDTAVYYCATYRSYVTPLDYWGQGTLVTVSS
```

Chain 2 (SEQ ID NO: 34) (underlined portions indicate CDR1, CDR2, CDR3):
DIQMTQSPSSLSASVGDRVTITCKSSQSLLYTSSQKNYLAWYQQKPGKAPKLLIYWASTRESGVP
SRFSGSGSGTDFTLTISSLQPEDFATYYCQQYYAYPWTFGQGTKVEIK CDR Sequences in SEQ ID Nos: 25-34
GFNIKDT (SEQ ID NO: 35)

YPTNGY (SEQ ID NO: 36)

WGGDGFYAMDY (SEQ ID NO: 37)

RASQDVNTAVA (SEQ ID NO: 38)

SASFLYS ((SEQ ID NO: 39)

QQHYTTPPT (SEQ ID NO: 40)

GFTFTDY (SEQ ID NO: 41)

NPNSGG (SEQ ID NO: 42)

NLGPSFYFDY (SEQ ID NO: 43)

KASQDVSIGVA (SEQ ID NO: 44)

SASYRYT (SEQ ID NO: 45)

QQYYIYPYT (SEQ ID NO: 46)

GFSLTNY (SEQ ID NO: 47)

WSGGN (SEQ ID NO: 48)

ALTYYDYEFAY (SEQ ID NO: 49)

RASQSIGTNIH (SEQ ID NO: 50)

YASESIS (SEQ ID NO: 51)

QQNNNWPTT (SEQ ID NO: 52)

GGSVSSGDY (SEQ ID NO: 53)

YYSGN (SEQ ID NO: 54)

DRVTGAFDI (SEQ ID NO: 55)

QASQDISNYLN (SEQ ID NO: 56)

DASNLET (SEQ ID NO: 57)

QHFDHLPLA (SEQ ID NO: 58)

GYTFTSY (SEQ ID NO: 59)

DPSNSD (SEQ ID NO: 60)

YRSYVTPLDY (SEQ ID NO: 61)

KSSQSLLYTSSQKNYLA (SEQ ID NO: 62)

WASTRES (SEQ ID NO: 63)

QQYYAYPWT (SEQ ID NO: 64)

The invention claimed is:

1. An antibody-drug conjugate (ADC) or a pharmaceutically acceptable salt thereof, comprising:
   a tetravalent monoclonal antibody conjugated to a cytotoxic drug by a chemical linker,
   wherein the monoclonal antibody comprises:
      two long chains and four short chains, wherein each of the long chains comprises a first segment and a second segment, the first segment located proximal to the N-terminus of the long chain, and the second segment located proximal to the C-terminus of the long chain, each of the first segment and second segment paring with one of the short chains to form an antigen-binding fragment domain, therefore forming four antigen-binding fragment domains having specificity toward a same antigen;
   and wherein:
      (a) each of the long chains comprises the sequence of SEQ ID NO:1 and each of the short chains comprises the sequence of SEQ ID NO:2; or
      (b) each of the long chains comprises the sequence of SEQ ID NO:13 and each of the short chains comprises the sequence of SEQ ID NO:14; or
      (c) each of the long chains comprises the sequence of SEQ ID NO:15 and each of the short chains comprises the sequence of SEQ ID NO:16; or
      (d) each of the long chains comprises the sequence of SEQ ID NO:17 and each of the short chains comprises the sequence of SEQ ID NO:18; or
      (e) each of the long chains comprises the sequence of SEQ ID NO:21 and each of the short chains comprises the sequence of SEQ ID NO:22; or
      (f) each of the long chains comprises the sequence of SEQ ID NO:23 and each of the short chains comprises the sequence of SEQ ID NO:24.

2. The ADC, or the pharmaceutically acceptable salt thereof, of claim 1, wherein the two long chains are identical, and wherein the four short chains are identical.

3. An ADC or a pharmaceutically acceptable salt thereof, comprising:
   a monoclonal antibody conjugated to a cytotoxic drug by a chemical linker, wherein the monoclonal antibody comprises two identical long chains and four identical short chains, wherein:
      (a) each of the long chains comprises the sequence of SEQ ID NO:1 and each of the short chains comprises the sequence of SEQ ID NO:2; or
      (b) each of the long chains comprises the sequence of SEQ ID NO:13 and each of the short chains comprises the sequence of SEQ ID NO:14; or
      (c) each of the long chains comprises the sequence of SEQ ID NO:15 and each of the short chains comprises the sequence of SEQ ID NO:16; or
      (d) each of the long chains comprises the sequence of SEQ ID NO:17 and each of the short chains comprises the sequence of SEQ ID NO:18; or
      (e) each of the long chains comprises the sequence of SEQ ID NO:21 and each of the short chains comprises the sequence of SEQ ID NO:22; or
      (f) each of the long chains comprises the sequence of SEQ ID NO:23 and each of the short chains comprises the sequence of SEQ ID NO:24.

4. The ADC, or the pharmaceutically acceptable salt thereof, of claim 1, wherein the cytotoxic drug is selected from the group consisting of monomethyl auristatin E (MMAE), monomethyl auristatin F (MMAF), auristatin E, auristatin F, maytansine DM1 and DM4, maytansinol, sandramycin, pyrrolobenzodiazepine dimer, anthracyclines, calicheamicin, dolastatin 10, duocarmycin, doxorubicin, thailanstatin A, uncialamycin, amanitins, ricin, diphtheria toxin, eribulin, $^{131}$I, interleukins, tumor necrosis factors, chemokines, and nanoparticles.

5. The ADC, or the pharmaceutically acceptable salt thereof, of claim 1, wherein the chemical linker comprises a portion which is selected from the group consisting of 6-maleimidocaproyl (MC), maleimidopropionyl (MP), valine-citrulline (val-cit), alanine-phenylalanine (ala-phe), p-aminobenzyloxycarbonyl (PAB), N-succinimidyl 4-(2-pyridylthio)valerate (SPP), N-succinimidyl 4-(N-maleimidomethyl)-cyclohexane-1-carboxylate (SMCC), N-succinimidyl (4-iodo-acetyl) aminobenzoate (STAB), 6-maleimidocaproyl-valine-citrulline-p-aminobenzyloxycarbonyl (MC-vc-PAB), Val-Cit-PABC, butanoate (SPDB), N-succinimidyl 3-(pyridin-2-yldithio)-propionate (SPDP), Phe-Lys(Fmoc)-PAB, Aloc-D-Ala-Phe-Lys(Aloc)-PAB-PNP, Boc-Phe-(Alloc)Lys-PAB-PNP, and perfluorophenyl 3-(pyridine-2-yldisulfanyl) propanoate.

6. The ADC, or the pharmaceutically acceptable salt thereof, of claim 1, wherein the chemical linker comprises a PEGn spacer wherein n is a whole number between 1 and 20.

7. The ADC, or the pharmaceutically acceptable salt thereof, of claim 6, wherein the chemical linker further comprises a valine-citrulline dipeptide linker connected to the PEGn spacer.

8. The ADC, or the pharmaceutically acceptable salt thereof, of claim 1, wherein the drug-to-antibody ratio is between 1 and 12 inclusive.

9. The ADC, or the pharmaceutically acceptable salt thereof, of claim 3, wherein the cytotoxic drug is selected from the group consisting of monomethyl auristatin E (MMAE), monomethyl auristatin F (MMAF), auristatin E, auristatin F, maytansine DM1 and DM4, maytansinol, sandramycin, pyrrolobenzodiazepine dimer, anthracyclines, calicheamicin, dolastatin 10, duocarmycin, doxorubicin, thailanstatin A, uncialamycin, amanitins, ricin, diphtheria toxin, eribulin, $^{131}$I, interleukins, tumor necrosis factors, chemokines, and nanoparticles.

10. The ADC, or the pharmaceutically acceptable salt thereof, of claim 3, wherein the chemical linker comprises a portion which is selected from the group consisting of 6-maleimidocaproyl (MC), maleimidopropionyl (MP), valine-citrulline (val-cit), alanine-phenylalanine (ala-phe), p-aminobenzyloxycarbonyl (PAB), N-succinimidyl 4-(2-pyridylthio)valerate (SPP), N-succinimidyl 4-(N-maleimidomethyl)-cyclohexane-1-carboxylate (SMCC), N-succinimidyl (4-iodo-acetyl) aminobenzoate (STAB), 6-maleimidocaproyl-valine-citrulline-p-aminobenzyloxycarbonyl (MC-vc-PAB), Val-Cit-PABC, N-succinimidyl-4-(2-pyridyldithio) butanoate (SPDB), N-succinimidyl 3-(pyridin-2-yldithio)-propionate (SPDP), Phe-Lys(Fmoc)-PAB, Aloc-D-Ala-Phe-Lys(Aloc)-PAB-PNP, Boc-Phe-(Alloc)Lys-PAB-PNP, and perfluorophenyl 3-(pyridine-2-yldisulfanyl) propanoate.

11. The ADC, or the pharmaceutically acceptable salt thereof, of claim 3, wherein the chemical linker comprises a PEGn spacer wherein n is a whole number between 1 and 20.

12. The ADC, or the pharmaceutically acceptable salt thereof, of claim 11, wherein the chemical linker further comprises a valine-citrulline dipeptide linker connected to the PEGn spacer.

13. The ADC, or the pharmaceutically acceptable salt thereof, of claim 3, wherein the drug-to-antibody ratio is between 1 and 12 inclusive.

* * * * *